United States Patent
Osumi et al.

(10) Patent No.: US 7,455,996 B2
(45) Date of Patent: Nov. 25, 2008

(54) SOYBEAN RAFFINOSE SYNTHASE AND A METHOD FOR PRODUCING RAFFINOSE

(75) Inventors: Chieko Osumi, Kawasaki (JP); Jinshi Nozaki, Kawasaki (JP); Takao Kida, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 722 days.

(21) Appl. No.: 11/034,848

(22) Filed: Jan. 14, 2005

(65) Prior Publication Data

US 2005/0118300 A1   Jun. 2, 2005

Related U.S. Application Data

(60) Division of application No. 09/425,055, filed on Oct. 22, 1999, now Pat. No. 6,891,084, which is a continuation of application No. PCT/JP97/03879, filed on Oct. 24, 1997, which is a continuation-in-part of application No. 08/846,234, filed on Apr. 28, 1997, now Pat. No. 6,166,292.

(30) Foreign Application Priority Data

Apr. 26, 1996 (JP) ................. 08-107682
Jul. 26, 1996 (JP) ................. 08-198079
Apr. 28, 1997 (JP) ................. 09-111124

(51) Int. Cl.
C12P 19/18 (2006.01)
C12N 1/20 (2006.01)
C12N 9/10 (2006.01)
C07H 21/04 (2006.01)

(52) U.S. Cl. ............................ 435/97; 435/41; 435/183; 435/193; 435/72; 536/23.2

(58) Field of Classification Search .................. None
See application file for complete search history.

(56) References Cited

U.S. PATENT DOCUMENTS

| | | | |
|---|---|---|---|
| 5,346,815 | A | 9/1994 | Krulwich et al. |
| 5,466,595 | A | 11/1995 | Jones et al. |
| 5,532,152 | A | 7/1996 | Cousens et al. |
| 5,538,886 | A | 7/1996 | Schlessinger et al. |
| 5,545,545 | A | 8/1996 | Gengenbach et al. |
| 5,573,939 | A | 11/1996 | Bavik et al. |
| 5,589,375 | A | 12/1996 | Ullrich et al. |
| 5,589,385 | A | 12/1996 | Ryan et al. |
| 6,166,292 | A | 12/2000 | Osumi et al. |
| 2005/0009165 | A1 | 1/2005 | Osumi et al. |

FOREIGN PATENT DOCUMENTS

| | | |
|---|---|---|
| EP | 0 849 359 | 6/1993 |
| WO | WO 93/02196 | 2/1993 |
| WO | WO 93/07742 | 4/1993 |
| WO | WO 93/19190 | 9/1993 |
| WO | WO 98/49273 | 5/1998 |

OTHER PUBLICATIONS

E. Lazar, et al., "Transforming Growth Factor α: Mutation of Aspartic Acid 47 and Leucine 48 Results in Different Biological Activities", Molecular and Cellular Biology, Mar. 1988, vol. 8, No. 3, pp. 1247-1252.
H. Guo et al., "Protein Tolerance to Random Amino Acid Change", Proc. Natl. Acad. Sci., Jun. 22, 2004, vol. 101, No. 25, pp. 9205-9210.
Notice of Reasons for Rejection issued in corresponding Japanese Patent Application No. 09-111124, Aug. 24, 2005 (w/English Translation).
I. Lehle, et al., "The Function of myo-Inositol in the Biosynthesis of Raffinose Purification and Characterization of Galactinol: Sucrose 6-Galactosyltransferase from Vicia Faba Seeds", Eur. J. Biochem., 1973, vol. 38, No. 1, pp. 103-110.
Hiroyuki Hashimoto, et al., "Synthesis of α-Galactosides with α-Galactosidase from Candida Guilliermondii H-404", Trends in Glycoscience and Glycotechnology, vol. 7, No. 34, pp. 149-158, Mar. 1995.
L.J. Sweetlove, et al., "Starch Metabolism in Tubers of Transgenic Potato (Solanum Tuberosum) With Increased Adpglucose Pyrophosphorylase", 1996, Biochem. J., vol. 320, pp. 493-498.
Y. Fujikura, et al., Accession No. S45033, Jan. 13, 1995.
G.R. Heck, et al., Accession No. S27762, Apr. 17, 1993.
Burgess et al,; Possible Dissociation of the Heparin-binding and Mitogenic Activities of Heparin-binding (Acidic Fibroblast) Growth . . . Mutagensis of a single Lysine Residue, 1990, Journal of Cell Biology, vol. 111:2129-2138.
GenBank Assession No. AAA32975, 1993.
Hill et al.; Functional Analysis of Conserved Histidines in ADP-Glucose Pyrophosphorylase from *Escherichia coli*, 1998, Biochemical and Biophysical Research Communication 244: 573-577.
Broun et al.; Catalytic Plasticity of Fatty Acid Modification Enzymes Underlying Chemical Diversity of Plant Lipids, 1998, Science, vol. 282: 1315-1317.
Bowie et al.; Deciphering the Message in Protein Sequences: Tolerance to Amino Acid Substitutions, 1990, Science, vol. 247: 1306-1310.

(Continued)

*Primary Examiner*—Rebecca E. Prouty
*Assistant Examiner*—Younus Meah
(74) *Attorney, Agent, or Firm*—Oblon, Spivak, McClelland, Maier & Neustadt, P.C.

(57) ABSTRACT

Raffinose is produced by allowing a raffinose synthase having the following properties to act on sucrose and galactinol:

(1) action and substrate specificity: produces raffinose from sucrose and galactinol;
(2) optimum pH: about 6 to 8;
(3) optimum temperature: about 35 to 40° C.;
(4) molecular weight:
  (i) about 75 kDa to 95 kDa estimated by gel filtration chromatography;
  (ii) about 90 kDa to 100 kDa estimated by polyacrylamide gel electrophoresis (Native PAGE); and
  (iii) about 90 kDa to 100 kDa estimated by SDS-polyacrylamide gel electrophoresis under a reduced condition (SDS-PAGE); and
(5) inhibition: inhibited by iodoacetamide, N-ethylmaleimide, and myo-inositol.

8 Claims, 7 Drawing Sheets

OTHER PUBLICATIONS

Heck et al (Apr. 1993, NCBI Database Accession No. M77475).
Peterbauer et al (1999, The Plant Journal 20(5):509-518).
Fourgoux-Nicol et al (1999, Plant Molecular Biology 40: 857-872).
McConnell et al (2001, Nature 411 (6838):709-713).
E.M. Castillo, et al., "Raffinose Synthase and Galactinol Synthase in Developing Seeds and Leaves of Legumes", J. Agric. Food Chem., vol. 38, No. 2, pp. 351-355, 1990.
G.R. Heck, et al., Ebi Database, AC Q40077, M77475, XP 002135516, Feb. 1922, "Seed Imbibition Protein", Nov. 1996.
F. Keller, et al., "Metabolism of Carbohydrates in Sinks and Sources: Galactosyl-Sucrose Oligosaccharides", Library of Congress Cataloging-in-Publication Data, pp. 157-183.
Ann de Clercq, et al., "Stable Accumulation of Modified 2S Albumin Seed Storage Proteins with Higher Methionine Contents in Transgenic Plants", Plant Physiol. (1990) 94, pp. 970-979.
C. Lacorte, et al., "Transient Expression of Gus and the 2Salbumin Gene From Brazil Nut I Peanut (*Arachis hyogaea* L.) Seed Explants Using Particle Bombardment", Plant Cell Reports, 1997, 16, pp. 619-623.
C.P. Ramono, et al., "Uncoupling Auxin and Ethylene Effects in Transgenic Tobacco and Arabidopsis Plants", Plant Cell, vol. 5, Feb. 1993, pp. 181-189, American Society of Plant Physiologists.
M.W. Lassner, et al., "A Jojoba Beta-Ketoacyl-COA Synthase cDNA Complements the Canola Fatty Acid Elongation Mutation in Transgenic Plants", The Plant Cell, vol. 8, Feb. 1996, pp. 281-292, American Society of Plant Physiologists.
C. Napoli, et al., "Introduction of a Chimeric Chalcone Synthase Gene Into Petunia Results in Reversible Co-Suppression of Homologous Genes in Trans", The Plant Cell, vol. 2, Apr. 1990, pp. 279-289, American Society of Plant Physiologists.
U.S. Appl. No. 11/034,484, filed Jan. 14, 2005, Osumi, et al.
U.S. Appl. No. 11/034,678, filed Jan. 14, 2005, Osumi, et al.
U.S. Appl. No. 10/948,251, filed Sep. 24, 2004, Osumi, et al.
U.S. Appl. No. 09/675,208, filed Sep. 29, 2000, Osumi, et al.

M  S

200 —

116 ▬

97.4 ▬ —

66 ▬

45 ▬

F I G. 2

(SEQ ID NO:6) A1  5'- TTY TAY CTB ACH GTN CAY CCT CA -3'
(SEQ ID NO:7) A2  5'- TTY TAY CTB ACH GTN CAY CCC CA -3'
(SEQ ID NO:8) A3  5'- TTY TAY CTB ACH GTN CAY CCA CA -3'
(SEQ ID NO:9) A4  5'- TTY TAY CTB ACH GTN CAY CCG CA -3'

Phe Gly Trp Cys Thr Trp Asp Ala Phe Tyr Val His Pro Gln Gly Val Ile Glu Gly Val Arg His Leu Val Asp Gly Gly Cys
(SEQ ID NO:1)

B1 5'- GAR GGN GTN MGN CAY CTR GTN GAY GG -3' (SEQ ID NO:10)
B2 5'- GAR GGN GTN MGN CAY CTY GTN GAY GG -3' (SEQ ID NO:11)
B3 5'- GAR GGN GTN MGN CAY TTR GTN GAY GG -3' (SEQ ID NO:12)

(SEQ ID NO:18) 3'- CTY CCN CAN KCI GTR GAY CAI CTR CC -5' B'1
(SEQ ID NO:19) 3'- CTY CCN CAN KCI GTR GAR CAI CTR CC -5' B'2
(SEQ ID NO:20) 3'- CTY CCN CAN KCI GTR TAY CAI CTR CC -5' B'3

D1  5'- TTY GAY GCN TCN GAR CCH GAY TCD CGN CA -3' (SEQ ID NO:13)
D2  5'- TTY GAY GCN TCN GAR CCH GAY TCD AGY CAY -3' (SEQ ID NO:14)

C1  5'- GTN GGN TGY TTY GTN GGY TTY GAY GC -3' (SEQ ID NO:15)
C2  5'- GTN GGN TGY TTY GTN GGR TTY GAY GC -3' (SEQ ID NO:16)

Pro Val Ser Val Gly Cys Phe Val Gly Phe Asp Ala Ser Glu Pro Asp Ser Arg His
(SEQ ID NO:2)

3'- AAR CTR CGN AGI CTY GGD CTR AGH GCI GT -5'  D'1 (SEQ ID NO:21)
3'- AAR CTR CGN AGI CTY GGD CTR AGH TCR GTR -5' D'2 (SEQ ID NO:22)

E  5'- CAY CAR GAY CTR ATG GTN GT -3' (SEQ ID NO:17)
   Tyr Asp Gln Asp Gln Met Val Val Val Gln Val Pro Trp Pro
   (SEQ ID NO:3)

SEQUENCE LISTING

```
<160> NUMBER OF SEQ ID NOS: 30

<210> SEQ ID NO 1
<211> LENGTH: 30
<212> TYPE: PRT
<213> ORGANISM: Cucumis sativus

<400> SEQUENCE: 1

Phe Gly Trp Cys Thr Trp Asp Ala Phe Tyr Leu Thr Val His Pro Gln
1               5                   10                  15

Gly Val Ile Glu Gly Val Arg His Leu Val Asp Gly Gly Cys
            20                  25                  30

<210> SEQ ID NO 2
<211> LENGTH: 19
<212> TYPE: PRT
<213> ORGANISM: Cucumis sativus

<400> SEQUENCE: 2

Pro Val Ser Val Gly Cys Phe Val Gly Phe Asp Ala Ser Glu Pro Asp
1               5                   10                  15

Ser Arg His

<210> SEQ ID NO 3
<211> LENGTH: 14
<212> TYPE: PRT
<213> ORGANISM: Cucumis sativus

<400> SEQUENCE: 3

Tyr Asp Gln Asp Gln Met Val Val Gln Val Pro Trp Pro
1               5                   10

<210> SEQ ID NO 4
<211> LENGTH: 2569
<212> TYPE: DNA
<213> ORGANISM: Cucumis sativus
<220> FEATURE:
<221> NAME/KEY: CDS
<222> LOCATION: (56)..(2407)
<223> OTHER INFORMATION:
```

<400> SEQUENCE: 4

```
aaaaaacaac ccttctttta gtttttggg tttgtttctt cttttcttct cacaa atg                      58
                                                                      Met
                                                                      1 gct cct agt ttt aaa aat ggt ggc tcc aac gta gtt tca ttt gat ggc                     106
Ala Pro Ser Phe Lys Asn Gly Gly Ser Asn Val Val Ser Phe Asp Gly
            5                  10                  15 tta aat gac atg tcg tca ccg ttt gca atc gac gga tcg gat ttc act                     154
Leu Asn Asp Met Ser Ser Pro Phe Ala Ile Asp Gly Ser Asp Phe Thr
         20                  25                  30 gtg aac ggt cat tcg ttt ctg tcc gat gtt cct gag aac att gtt gct                     202
Val Asn Gly His Ser Phe Leu Ser Asp Val Pro Glu Asn Ile Val Ala
     35                  40                  45 tct cct tct ccg tac act tcg ata gac aag tcc ccg gtt tcg gtt ggt                     250
Ser Pro Ser Pro Tyr Thr Ser Ile Asp Lys Ser Pro Val Ser Val Gly
 50                  55                  60                  65 tgc ttt gtt gga ttc gac gcg tcg gaa cct gat agc cga cat gtt gtt                     298
Cys Phe Val Gly Phe Asp Ala Ser Glu Pro Asp Ser Arg His Val Val
                 70                  75                  80 tcg att ggg aag ctg aag gat att cgg ttt atg agt att ttc agg ttt                     346
Ser Ile Gly Lys Leu Lys Asp Ile Arg Phe Met Ser Ile Phe Arg Phe
             85                  90                  95 aag gtt tgg tgg act aca cac tgg gtt ggt cga aat ggt ggg gat ctt                     394
Lys Val Trp Trp Thr Thr His Trp Val Gly Arg Asn Gly Gly Asp Leu
        100                 105                 110 gaa tcg gag act cag att gtg atc ctt gag aag tca gat tct ggt cga                     442
Glu Ser Glu Thr Gln Ile Val Ile Leu Glu Lys Ser Asp Ser Gly Arg
    115                 120                 125 ccg tat gtt ttc ctt ctt ccg atc gtt gag gga ccg ttc cga acc tcg                     490
Pro Tyr Val Phe Leu Leu Pro Ile Val Glu Gly Pro Phe Arg Thr Ser
130                 135                 140                 145 att cag cct ggg gat gat gac ttt gtc gat gtt tgt gtc gag agt ggt                     538
Ile Gln Pro Gly Asp Asp Asp Phe Val Asp Val Cys Val Glu Ser Gly
                150                 155                 160 tcg tcg aaa gtt gtt gat gca tcg ttc cga agt atg ttg tat ctt cat                     586
Ser Ser Lys Val Val Asp Ala Ser Phe Arg Ser Met Leu Tyr Leu His
            165                 170                 175 gct ggt gat gat ccg ttt gca ctt gtt aaa gag gcg atg aag atc gtg                     634
Ala Gly Asp Asp Pro Phe Ala Leu Val Lys Glu Ala Met Lys Ile Val
        180                 185                 190 agg acc cat ctt gga act ttt cgc ttg ttg gag gag aag act cca cca                     682
Arg Thr His Leu Gly Thr Phe Arg Leu Leu Glu Glu Lys Thr Pro Pro
    195                 200                 205 ggt atc gtg gac aaa ttc ggt tgg tgc acg tgg gac gcg ttt tac cta                     730
Gly Ile Val Asp Lys Phe Gly Trp Cys Thr Trp Asp Ala Phe Tyr Leu
210                 215                 220                 225 acg gtt cat cca cag ggc gta ata gaa ggc gtg agg cat ctc gtc gac                     778
Thr Val His Pro Gln Gly Val Ile Glu Gly Val Arg His Leu Val Asp
                230                 235                 240 ggc ggt tgt cct ccc ggt tta gtc cta atc gac gat ggt tgg caa tcc                     826
Gly Gly Cys Pro Pro Gly Leu Val Leu Ile Asp Asp Gly Trp Gln Ser
            245                 250                 255 atc gga cac gat tcg gat ccc atc acc aaa gaa gga atg aac caa acc                     874
Ile Gly His Asp Ser Asp Pro Ile Thr Lys Glu Gly Met Asn Gln Thr
        260                 265                 270 gtc gcc ggc gag caa atg ccc tgc cgt ctt ttg aaa ttc caa gag aat                     922
Val Ala Gly Glu Gln Met Pro Cys Arg Leu Leu Lys Phe Gln Glu Asn
    275                 280                 285
```

```
                                                    -continued tac aaa ttc cgt gac tac gtc aat ccc aag gcc acc ggc ccc cga gcc     970
Tyr Lys Phe Arg Asp Tyr Val Asn Pro Lys Ala Thr Gly Pro Arg Ala
290                 295                 300                 305 ggc cag aag ggg atg aag gcg ttt ata gat gaa ctc aaa gga gag ttt    1018
Gly Gln Lys Gly Met Lys Ala Phe Ile Asp Glu Leu Lys Gly Glu Phe
                    310                 315                 320 aag act gtg gag cat gtt tat gtt tgg cat gct ttg tgt gga tat tgg   1066
Lys Thr Val Glu His Val Tyr Val Trp His Ala Leu Cys Gly Tyr Trp
                325                 330                 335 ggt ggc ctt cgc ccg cag gtg cct ggc ttg cct gag gca cgt gtg att   1114
Gly Gly Leu Arg Pro Gln Val Pro Gly Leu Pro Glu Ala Arg Val Ile
            340                 345                 350 cag cca gtg ctt tca cca ggg ctg cag atg acg atg gag gat ttg gcg   1162
Gln Pro Val Leu Ser Pro Gly Leu Gln Met Thr Met Glu Asp Leu Ala
355                 360                 365 gtg gat aag att gtt ctt cat aag gtc ggg ctg gtc ccg ccg gag aag   1210
Val Asp Lys Ile Val Leu His Lys Val Gly Leu Val Pro Pro Glu Lys
370                 375                 380                 385 gct gag gag atg tac gaa gga ctt cat gct cat ttg gaa aaa gtt ggg   1258
Ala Glu Glu Met Tyr Glu Gly Leu His Ala His Leu Glu Lys Val Gly
                    390                 395                 400 atc gac ggt gtt aag att gac gtt atc cac cta ttg gag atg ttg tgt   1306
Ile Asp Gly Val Lys Ile Asp Val Ile His Leu Leu Glu Met Leu Cys
                405                 410                 415 gaa gac tat gga ggg aga gtg gat ttg gca aag gca tat tac aaa gca   1354
Glu Asp Tyr Gly Gly Arg Val Asp Leu Ala Lys Ala Tyr Tyr Lys Ala
            420                 425                 430 atg acc aaa tca ata aat aaa cat ttt aaa gga aat gga gtc att gca   1402
Met Thr Lys Ser Ile Asn Lys His Phe Lys Gly Asn Gly Val Ile Ala
435                 440                 445 agt atg gaa cat tgt aac gac ttc atg ttc ctt ggc acg gaa gct atc   1450
Ser Met Glu His Cys Asn Asp Phe Met Phe Leu Gly Thr Glu Ala Ile
450                 455                 460                 465 tct ctt ggt cgt gtt ggt gat gac ttt tgg tgc acg gac ccc tct ggt   1498
Ser Leu Gly Arg Val Gly Asp Asp Phe Trp Cys Thr Asp Pro Ser Gly
                    470                 475                 480 gat cca aac ggt acg ttt tgg ctc caa gga tgt cac atg gtt cat tgt   1546
Asp Pro Asn Gly Thr Phe Trp Leu Gln Gly Cys His Met Val His Cys
                485                 490                 495 gcc aac gac agc ttg tgg atg ggg aac ttc atc cac cct gac tgg gat   1594
Ala Asn Asp Ser Leu Trp Met Gly Asn Phe Ile His Pro Asp Trp Asp
            500                 505                 510 atg ttc caa tcc acc cac cct tgt gcc gcc ttc cat gct gcc tct cga   1642
Met Phe Gln Ser Thr His Pro Cys Ala Ala Phe His Ala Ala Ser Arg
515                 520                 525 gcc atc tct ggt ggc ccg atc tat gtt agt gat tct gtg gga aag cat   1690
Ala Ile Ser Gly Gly Pro Ile Tyr Val Ser Asp Ser Val Gly Lys His
530                 535                 540                 545 aac ttt gat ctt ctg aaa aaa cta gtg ctt cct gat gga tcg atc ctt   1738
Asn Phe Asp Leu Leu Lys Lys Leu Val Leu Pro Asp Gly Ser Ile Leu
                    550                 555                 560 cga agt gag tac tat gca ctc ccg act cgc gat tgt ttg ttt gaa gac   1786
Arg Ser Glu Tyr Tyr Ala Leu Pro Thr Arg Asp Cys Leu Phe Glu Asp
                565                 570                 575 cct ttg cat aat gga gaa act atg ctt aag att tgg aat ctc aac aag   1834
Pro Leu His Asn Gly Glu Thr Met Leu Lys Ile Trp Asn Leu Asn Lys
            580                 585                 590 ttc act gga gtg att ggt gca ttc aac tgc caa gga gga gga tgg tgt   1882
Phe Thr Gly Val Ile Gly Ala Phe Asn Cys Gln Gly Gly Gly Trp Cys
595                 600                 605
```

-continued

```
cgt gag aca cgc cgc aac caa tgc ttt tca caa tac tca aaa cga gtg    1930
Arg Glu Thr Arg Arg Asn Gln Cys Phe Ser Gln Tyr Ser Lys Arg Val
610             615                 620                 625 aca tcc aaa act aac cca aaa gac ata gaa tgg cac agt gga gaa aac    1978
Thr Ser Lys Thr Asn Pro Lys Asp Ile Glu Trp His Ser Gly Glu Asn
                630                 635                 640 cct atc tct att gaa ggc gtt aaa acc ttt gcg ctt tac ctc tat caa    2026
Pro Ile Ser Ile Glu Gly Val Lys Thr Phe Ala Leu Tyr Leu Tyr Gln
            645                 650                 655 gcc aaa aaa ctt atc ctc tcc aag ccc tct caa gat ctt gac ata gct    2074
Ala Lys Lys Leu Ile Leu Ser Lys Pro Ser Gln Asp Leu Asp Ile Ala
        660                 665                 670 ctt gac cca ttc gaa ttc gag ctc atc act gtt tca cca gtg acc aaa    2122
Leu Asp Pro Phe Glu Phe Glu Leu Ile Thr Val Ser Pro Val Thr Lys
    675                 680                 685 ctc atc caa act tct cta cac ttt gcc cca att ggg ctg gtg aac atg    2170
Leu Ile Gln Thr Ser Leu His Phe Ala Pro Ile Gly Leu Val Asn Met
690                 695                 700                 705 ctt aac act agt gga gcc atc caa tct gtg gac tat gac gat gac cta    2218
Leu Asn Thr Ser Gly Ala Ile Gln Ser Val Asp Tyr Asp Asp Asp Leu
                710                 715                 720 agc tca gtc gag att ggt gtc aaa ggg tgt ggt gag atg cga gta ttt    2266
Ser Ser Val Glu Ile Gly Val Lys Gly Cys Gly Glu Met Arg Val Phe
            725                 730                 735 gca tcg aaa aaa cca agg gct tgt cgt att gat ggg gag gat gtt ggg    2314
Ala Ser Lys Lys Pro Arg Ala Cys Arg Ile Asp Gly Glu Asp Val Gly
        740                 745                 750 ttc aag tat gat cag gac caa atg gtg gtg gtt caa gtg cca tgg cca    2362
Phe Lys Tyr Asp Gln Asp Gln Met Val Val Val Gln Val Pro Trp Pro
    755                 760                 765 att gat tct tca tcg ggt ggc att tcg gtt atc gag tac ttg ttt        2407
Ile Asp Ser Ser Ser Gly Gly Ile Ser Val Ile Glu Tyr Leu Phe
770                 775                 780 taatttttat ttatgtarag ctcaatgatt gttgttgttg tcgctgttgt tgctatcaat   2467
gtatttctct ccaaaagaaa attatgtgta atttggagag taattaagtg agtkaaattt   2527 taaataaarac tacttttaat tatttatcaa aaaaaaaaaa aa                     2569

<210> SEQ ID NO 5
<211> LENGTH: 784
<212> TYPE: PRT
<213> ORGANISM: Cucumis sativus

<400> SEQUENCE: 5

Met Ala Pro Ser Phe Lys Asn Gly Gly Ser Asn Val Val Ser Phe Asp
1               5                   10                  15

Gly Leu Asn Asp Met Ser Ser Pro Phe Ala Ile Asp Gly Ser Asp Phe
            20                  25                  30

Thr Val Asn Gly His Ser Phe Leu Ser Asp Val Pro Glu Asn Ile Val
        35                  40                  45

Ala Ser Pro Ser Pro Tyr Thr Ser Ile Asp Lys Ser Pro Val Ser Val
    50                  55                  60

Gly Cys Phe Val Gly Phe Asp Ala Ser Glu Pro Asp Ser Arg His Val
65                  70                  75                  80

Val Ser Ile Gly Lys Leu Lys Asp Ile Arg Phe Met Ser Ile Phe Arg
                85                  90                  95

Phe Lys Val Trp Trp Thr Thr His Trp Val Gly Arg Asn Gly Gly Asp
            100                 105                 110
```

-continued

```
Leu Glu Ser Glu Thr Gln Ile Val Ile Leu Glu Lys Ser Asp Ser Gly
            115                 120                 125

Arg Pro Tyr Val Phe Leu Leu Pro Ile Val Glu Gly Pro Phe Arg Thr
        130                 135                 140

Ser Ile Gln Pro Gly Asp Asp Phe Val Asp Val Cys Val Glu Ser
145                 150                 155                 160

Gly Ser Ser Lys Val Val Asp Ala Ser Phe Arg Ser Met Leu Tyr Leu
                165                 170                 175

His Ala Gly Asp Asp Pro Phe Ala Leu Val Lys Glu Ala Met Lys Ile
            180                 185                 190

Val Arg Thr His Leu Gly Thr Phe Arg Leu Leu Glu Glu Lys Thr Pro
        195                 200                 205

Pro Gly Ile Val Asp Lys Phe Gly Trp Cys Thr Trp Asp Ala Phe Tyr
    210                 215                 220

Leu Thr Val His Pro Gln Gly Val Ile Glu Gly Val Arg His Leu Val
225                 230                 235                 240

Asp Gly Gly Cys Pro Pro Gly Leu Val Leu Ile Asp Asp Gly Trp Gln
                245                 250                 255

Ser Ile Gly His Asp Ser Asp Pro Ile Thr Lys Glu Gly Met Asn Gln
            260                 265                 270

Thr Val Ala Gly Glu Gln Met Pro Cys Arg Leu Leu Lys Phe Gln Glu
        275                 280                 285

Asn Tyr Lys Phe Arg Asp Tyr Val Asn Pro Lys Ala Thr Gly Pro Arg
    290                 295                 300

Ala Gly Gln Lys Gly Met Lys Ala Phe Ile Asp Glu Leu Lys Gly Glu
305                 310                 315                 320

Phe Lys Thr Val Glu His Val Tyr Val Trp His Ala Leu Cys Gly Tyr
                325                 330                 335

Trp Gly Gly Leu Arg Pro Gln Val Pro Gly Leu Pro Glu Ala Arg Val
            340                 345                 350

Ile Gln Pro Val Leu Ser Pro Gly Leu Gln Met Thr Met Glu Asp Leu
        355                 360                 365

Ala Val Asp Lys Ile Val Leu His Lys Val Gly Leu Val Pro Pro Glu
    370                 375                 380

Lys Ala Glu Glu Met Tyr Glu Gly Leu His Ala His Leu Glu Lys Val
385                 390                 395                 400

Gly Ile Asp Gly Val Lys Ile Asp Val Ile His Leu Leu Glu Met Leu
                405                 410                 415

Cys Glu Asp Tyr Gly Gly Arg Val Asp Leu Ala Lys Ala Tyr Tyr Lys
            420                 425                 430

Ala Met Thr Lys Ser Ile Asn Lys His Phe Lys Gly Asn Gly Val Ile
        435                 440                 445

Ala Ser Met Glu His Cys Asn Asp Phe Met Phe Leu Gly Thr Glu Ala
    450                 455                 460

Ile Ser Leu Gly Arg Val Gly Asp Asp Phe Trp Cys Thr Asp Pro Ser
465                 470                 475                 480

Gly Asp Pro Asn Gly Thr Phe Trp Leu Gln Gly Cys His Met Val His
                485                 490                 495

Cys Ala Asn Asp Ser Leu Trp Met Gly Asn Phe Ile His Pro Asp Trp
            500                 505                 510

Asp Met Phe Gln Ser Thr His Pro Cys Ala Ala Phe His Ala Ala Ser
        515                 520                 525
```

```
Arg Ala Ile Ser Gly Gly Pro Ile Tyr Val Ser Asp Ser Val Gly Lys
    530                 535                 540

His Asn Phe Asp Leu Leu Lys Lys Leu Val Leu Pro Asp Gly Ser Ile
545                 550                 555                 560

Leu Arg Ser Glu Tyr Tyr Ala Leu Pro Thr Arg Asp Cys Leu Phe Glu
                565                 570                 575

Asp Pro Leu His Asn Gly Glu Thr Met Leu Lys Ile Trp Asn Leu Asn
            580                 585                 590

Lys Phe Thr Gly Val Ile Gly Ala Phe Asn Cys Gln Gly Gly Gly Trp
        595                 600                 605

Cys Arg Glu Thr Arg Arg Asn Gln Cys Phe Ser Gln Tyr Ser Lys Arg
    610                 615                 620

Val Thr Ser Lys Thr Asn Pro Lys Asp Ile Glu Trp His Ser Gly Glu
625                 630                 635                 640

Asn Pro Ile Ser Ile Glu Gly Val Lys Thr Phe Ala Leu Tyr Leu Tyr
                645                 650                 655

Gln Ala Lys Lys Leu Ile Leu Ser Lys Pro Ser Gln Asp Leu Asp Ile
            660                 665                 670

Ala Leu Asp Pro Phe Glu Phe Glu Leu Ile Thr Val Ser Pro Val Thr
        675                 680                 685

Lys Leu Ile Gln Thr Ser Leu His Phe Ala Pro Ile Gly Leu Val Asn
690                 695                 700

Met Leu Asn Thr Ser Gly Ala Ile Gln Ser Val Asp Tyr Asp Asp Asp
705                 710                 715                 720

Leu Ser Ser Val Glu Ile Gly Val Lys Gly Cys Gly Glu Met Arg Val
                725                 730                 735

Phe Ala Ser Lys Lys Pro Arg Ala Cys Arg Ile Asp Gly Glu Asp Val
            740                 745                 750

Gly Phe Lys Tyr Asp Gln Asp Gln Met Val Val Val Gln Val Pro Trp
        755                 760                 765

Pro Ile Asp Ser Ser Ser Gly Gly Ile Ser Val Ile Glu Tyr Leu Phe
770                 775                 780
```

```
<210> SEQ ID NO 6
<211> LENGTH: 23
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (15)..(15)
<223> OTHER INFORMATION: n is a, c, g, or t

<400> SEQUENCE: 6
ttytayctba chgtncaycc tca                                              23

<210> SEQ ID NO 7
<211> LENGTH: 23
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (15)..(15)
<223> OTHER INFORMATION: n is a, c, g, or t

<400> SEQUENCE: 7
ttytayctba chgtncaycc cca                                              23
```

<210> SEQ ID NO 8
<211> LENGTH: 23
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (15)..(15)
<223> OTHER INFORMATION: n is a, c, g, or t

<400> SEQUENCE: 8
ttytayctba chgtncaycc aca                                              23

<210> SEQ ID NO 9
<211> LENGTH: 23
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (15)..(15)
<223> OTHER INFORMATION: n is a, c, g, or t

<400> SEQUENCE: 9
ttytayctba chgtncaycc gca                                              23

<210> SEQ ID NO 10
<211> LENGTH: 26
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (6)..(6)
<223> OTHER INFORMATION: n is I
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is I
<220> FEATURE:
<221> NAME/KEY: misc_feature
<222> LOCATION: (21)..(21)
<223> OTHER INFORMATION: n is a, c, g, or t

<400> SEQUENCE: 10
garggngtnm gncayctrgt ngaygg                                           26

<210> SEQ ID NO 11
<211> LENGTH: 26
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (6)..(6)
<223> OTHER INFORMATION: n is I
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)

<223> OTHER INFORMATION: n is I
<220> FEATURE:
<221> NAME/KEY: misc_feature
<222> LOCATION: (21)..(21)
<223> OTHER INFORMATION: n is a, c, g, or t

<400> SEQUENCE: 11
garggngtnm gncayctygt ngaygg                                              26

<210> SEQ ID NO 12
<211> LENGTH: 26
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (6)..(6)
<223> OTHER INFORMATION: n is I
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is I
<220> FEATURE:
<221> NAME/KEY: misc_feature
<222> LOCATION: (21)..(21)
<223> OTHER INFORMATION: n is a, c, g, or t

<400> SEQUENCE: 12
garggngtnm gncayttrgt ngaygg                                              26

<210> SEQ ID NO 13
<211> LENGTH: 26
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (3)..(3)
<223> OTHER INFORMATION: n = I
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 13
gtnggntgyt tygtnggytt ygaygc                                              26

<210> SEQ ID NO 14
<211> LENGTH: 26
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (3)..(3)
<223> OTHER INFORMATION: n is I
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature

```
<222> LOCATION: (15)..(15)
<223> OTHER INFORMATION: n is a, c, g, or t

<400> SEQUENCE: 14
gtnggntgyt tygtnggrtt ygaygc                                           26

<210> SEQ ID NO 15
<211> LENGTH: 29
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (9)..(9)
<223> OTHER INFORMATION: n is I
<220> FEATURE:
<221> NAME/KEY: misc_feature
<222> LOCATION: (12)..(12)
<223> OTHER INFORMATION: n is I
<220> FEATURE:
<221> NAME/KEY: misc_feature
<222> LOCATION: (27)..(27)
<223> OTHER INFORMATION: n is a, c, g, or t

<400> SEQUENCE: 15
ttygaygcnt cngarcchga ytcdcgnca                                        29

<210> SEQ ID NO 16
<211> LENGTH: 30
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (9)..(9)
<223> OTHER INFORMATION: n is I
<220> FEATURE:
<221> NAME/KEY: misc_feature
<222> LOCATION: (12)..(12)
<223> OTHER INFORMATION: n is I

<400> SEQUENCE: 16
ttygaygcnt cngarcchga ytcdagycay                                       30

<210> SEQ ID NO 17
<211> LENGTH: 20
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (18)..(18)
<223> OTHER INFORMATION: n is any nucleotide

<400> SEQUENCE: 17
gaycargayc tratggtngt                                                  20

<210> SEQ ID NO 18
<211> LENGTH: 26
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (6)..(6)
<223> OTHER INFORMATION: n is I
<220> FEATURE:
```

```
<221> NAME/KEY: misc_feature
<222> LOCATION: (15)..(15)
<223> OTHER INFORMATION: n is I
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 18
ccrtcnacya grtgncknac nccytc                                        26

<210> SEQ ID NO 19
<211> LENGTH: 26
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (6)..(6)
<223> OTHER INFORMATION: n is I
<220> FEATURE:
<221> NAME/KEY: misc_feature
<222> LOCATION: (15)..(15)
<223> OTHER INFORMATION: n is I
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 19
ccrtcnacra grtgncknac nccytc                                        26

<210> SEQ ID NO 20
<211> LENGTH: 26
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (6)..(6)
<223> OTHER INFORMATION: n is I
<220> FEATURE:
<221> NAME/KEY: misc_feature
<222> LOCATION: (15)..(15)
<223> OTHER INFORMATION: n is I
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 20
ccrtcnacya trtgncknac nccytc                                        26

<210> SEQ ID NO 21
<211> LENGTH: 29
<212> TYPE: DNA
<213> ORGANISM: Artificial Sequence
<220> FEATURE:
<223> OTHER INFORMATION: Synthetic DNA
```

-continued

```
<220> FEATURE:
<221> NAME/KEY: misc_feature
<222> LOCATION: (3)..(3)
<223> OTHER INFORMATION: n is I
<220> FEATURE:
<221> NAME/KEY: misc_feature
<222> LOCATION: (18)..(18)
<223> OTHER INFORMATION: n is I
<220> FEATURE:
<221> NAME/KEY: misc_feature
<222> LOCATION: (21)..(21)
<223> OTHER INFORMATION: n is a, c, g, or t

<400> SEQUENCE: 21
tgncghgart cdggytcnga ngcrtcraa                                       29

<210> SEQ ID NO 22
<211> LENGTH: 30
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (19)..(19)
<223> OTHER INFORMATION: n is I
<220> FEATURE:
<221> NAME/KEY: misc_feature
<222> LOCATION: (22)..(22)
<223> OTHER INFORMATION: n is a, c, g, or t

<400> SEQUENCE: 22
rtgrcthgar tcdggytcng angcrtcraa                                      30

<210> SEQ ID NO 23
<211> LENGTH: 2780
<212> TYPE: DNA
<213> ORGANISM: Glycine max cv. Clark63
<220> FEATURE:
<221> NAME/KEY: CDS
<222> LOCATION: (156)..(2405)
<223> OTHER INFORMATION:

<400> SEQUENCE: 23
tcttccattg gaggaccatt tcctcctgga atagaaatac taccacactt ttctttttc     60 acttctctaa gttgctaagt taattgctcc ttcatttttt cactcttcgt tctcgcgtac    120
ccgtgtcacg gtaactcgtg gtgaagtgtt cgaaa atg act gtc aca cct aag      173
                                      Met Thr Val Thr Pro Lys
                                      1               5 atc tca gtt aac gat ggg aaa ctt gtt gtc cat ggt aag acc att ctg      221
Ile Ser Val Asn Asp Gly Lys Leu Val Val His Gly Lys Thr Ile Leu
        10                  15                  20 act gga gtg cca gac aac gtt gtg ctg act cca ggt tct gga agg ggt      269
Thr Gly Val Pro Asp Asn Val Val Leu Thr Pro Gly Ser Gly Arg Gly
    25                  30                  35 ctt gtg act ggt gct ttt gtt ggt gcc aca gct tca cac agc aaa agt      317
Leu Val Thr Gly Ala Phe Val Gly Ala Thr Ala Ser His Ser Lys Ser
40                  45                  50 ctc cat gtg ttt cca atg ggt gtt tta gag ggg ctc cgg ttc atg tgt      365
Leu His Val Phe Pro Met Gly Val Leu Glu Gly Leu Arg Phe Met Cys
55                  60                  65                  70 tgt ttc cgg ttc aag tta tgg tgg atg act cag aga atg gga act tgt      413
Cys Phe Arg Phe Lys Leu Trp Trp Met Thr Gln Arg Met Gly Thr Cys
                75                  80                  85 ggg agg gat gtt cct ctg gag act caa ttc atg ctt att gag agc aaa      461
Gly Arg Asp Val Pro Leu Glu Thr Gln Phe Met Leu Ile Glu Ser Lys
```

-continued

```
                     90                  95                 100
gag agt gaa act gat ggg gag aat tct cca atc atc tac act gtc ttg      509
Glu Ser Glu Thr Asp Gly Glu Asn Ser Pro Ile Ile Tyr Thr Val Leu
        105                 110                 115 ctt cct ctc ctc gaa ggt caa ttc cga gct gtt ctt caa ggc aat gac      557
Leu Pro Leu Leu Glu Gly Gln Phe Arg Ala Val Leu Gln Gly Asn Asp
120                 125                 130 aag aac gag ata gag att tgc ctc gag agt ggg gat aat gca gtt gag      605
Lys Asn Glu Ile Glu Ile Cys Leu Glu Ser Gly Asp Asn Ala Val Glu
135                 140                 145                 150 act gac caa ggc ctt cac atg gtt tac atg cat gct ggg acc aat ccc      653
Thr Asp Gln Gly Leu His Met Val Tyr Met His Ala Gly Thr Asn Pro
            155                 160                 165 ttt gaa gtc atc aat caa gct gtc aag gct gtg gaa aaa cac atg caa      701
Phe Glu Val Ile Asn Gln Ala Val Lys Ala Val Glu Lys His Met Gln
                170                 175                 180 act ttt ctt cat cgt gag aag aaa agg ttg cca tct tgt ctt gac tgg      749
Thr Phe Leu His Arg Glu Lys Lys Arg Leu Pro Ser Cys Leu Asp Trp
                    185                 190                 195 ttt gga tgg tgc aca tgg gat gct ttc tat act gat gtc aca gct gag      797
Phe Gly Trp Cys Thr Trp Asp Ala Phe Tyr Thr Asp Val Thr Ala Glu
200                 205                 210 ggt gtt gag gaa ggc ctg aaa agt cta tca cag gga ggt aca cct cca      845
Gly Val Glu Glu Gly Leu Lys Ser Leu Ser Gln Gly Gly Thr Pro Pro
215                 220                 225                 230 cga ttc ctc atc ata gat gat ggt tgg caa cag att gaa aat aaa gca      893
Arg Phe Leu Ile Ile Asp Asp Gly Trp Gln Gln Ile Glu Asn Lys Ala
            235                 240                 245 aag gat gct act gaa tgt ttg gta caa gaa gga gca cag ttt gct act      941
Lys Asp Ala Thr Glu Cys Leu Val Gln Glu Gly Ala Gln Phe Ala Thr
                250                 255                 260 agg ttg act ggt att aaa gag aat act aaa ttt caa aag aaa tta cag      989
Arg Leu Thr Gly Ile Lys Glu Asn Thr Lys Phe Gln Lys Lys Leu Gln
                    265                 270                 275 aac aat gag cag atg tca ggt ctg aag cat cta gta cat gga gca aag      1037
Asn Asn Glu Gln Met Ser Gly Leu Lys His Leu Val His Gly Ala Lys
280                 285                 290 cag cat cac aat gtg aaa aat gta tat gta tgg cat gca cta gct ggt      1085
Gln His His Asn Val Lys Asn Val Tyr Val Trp His Ala Leu Ala Gly
295                 300                 305                 310 tat tgg ggt gga gtg aag cca gca gca acc ggc atg gaa cat tat gac      1133
Tyr Trp Gly Gly Val Lys Pro Ala Ala Thr Gly Met Glu His Tyr Asp
            315                 320                 325 act gcc ttg gca tat cca gtg cag tca cca ggc gtg cta gga aac caa      1181
Thr Ala Leu Ala Tyr Pro Val Gln Ser Pro Gly Val Leu Gly Asn Gln
                330                 335                 340 cca gac att gtc atg gac agc ttg gct gta cat ggc ttg ggc cta gtg      1229
Pro Asp Ile Val Met Asp Ser Leu Ala Val His Gly Leu Gly Leu Val
                    345                 350                 355 cac cca aag aag gtt ttc aat ttc tac aac gag ctc cat gct tac tta      1277
His Pro Lys Lys Val Phe Asn Phe Tyr Asn Glu Leu His Ala Tyr Leu
360                 365                 370 gct tct tgt gga gta gat gga gtg aag gtt gat gtg cag aac att att      1325
Ala Ser Cys Gly Val Asp Gly Val Lys Val Asp Val Gln Asn Ile Ile
375                 380                 385                 390 gag acc ctt ggt gcg gga cat ggt ggc cga gtg tca ctt act cgc agc      1373
Glu Thr Leu Gly Ala Gly His Gly Gly Arg Val Ser Leu Thr Arg Ser
            395                 400                 405 tat cat cac gcg ctt gag gct tcc att gct agc aat ttt act gat aac      1421
```

-continued

```
              Tyr His His Ala Leu Glu Ala Ser Ile Ala Ser Asn Phe Thr Asp Asn
                      410                 415                 420 gga tgc att gcg tgt atg tgt cac aac act gat gga ctt tat agt gct            1469
Gly Cys Ile Ala Cys Met Cys His Asn Thr Asp Gly Leu Tyr Ser Ala
            425                 430                 435 aag cag act gct att gtg aga gct tct gat gat ttt tac cct cgt gat            1517
Lys Gln Thr Ala Ile Val Arg Ala Ser Asp Asp Phe Tyr Pro Arg Asp
    440                 445                 450 cct gct tcc cat acc atc cat att tct tct gtt gca tac aac tca cta            1565
Pro Ala Ser His Thr Ile His Ile Ser Ser Val Ala Tyr Asn Ser Leu
455                 460                 465                 470 ttc ctt gga gaa ttc atg caa cct gac tgg gac atg ttt cat agt tta            1613
Phe Leu Gly Glu Phe Met Gln Pro Asp Trp Asp Met Phe His Ser Leu
                475                 480                 485 cac cca gca gca gat tat cat gct gca gct cgt gca att ggt gga tgt            1661
His Pro Ala Ala Asp Tyr His Ala Ala Ala Arg Ala Ile Gly Gly Cys
        490                 495                 500 cct att tat gtt agt gac aag cca ggc aat cac aat ttt gat ctt ctt            1709
Pro Ile Tyr Val Ser Asp Lys Pro Gly Asn His Asn Phe Asp Leu Leu
    505                 510                 515 aag aag ctg gtt ctc ccg gat ggt tcg gtt ctc cgt gct cag tta cct            1757
Lys Lys Leu Val Leu Pro Asp Gly Ser Val Leu Arg Ala Gln Leu Pro
520                 525                 530 ggc agg cca act cgt gat tct cta ttt gtg gat cca gcc aga gat agg            1805
Gly Arg Pro Thr Arg Asp Ser Leu Phe Val Asp Pro Ala Arg Asp Arg
535                 540                 545                 550 act agc ttg ctc aaa ata tgg aac ctg aac aaa tgc tct gga gtt gtt            1853
Thr Ser Leu Leu Lys Ile Trp Asn Leu Asn Lys Cys Ser Gly Val Val
                555                 560                 565 ggt gta ttt aac tgc caa ggt gct gga tgg tgc aag ata gag aag aaa            1901
Gly Val Phe Asn Cys Gln Gly Ala Gly Trp Cys Lys Ile Glu Lys Lys
        570                 575                 580 acc cgc atc cat gat aca tct cct ggt aca ctc acc gcc tct gtc tgc            1949
Thr Arg Ile His Asp Thr Ser Pro Gly Thr Leu Thr Ala Ser Val Cys
    585                 590                 595 gcc tct gat gtt gac ctc atc aca caa gta gca ggt gct gaa tgg ctt            1997
Ala Ser Asp Val Asp Leu Ile Thr Gln Val Ala Gly Ala Glu Trp Leu
600                 605                 610 gga gat aca att gtt tat gct tac aga tca ggt gag gtg att cgg cta            2045
Gly Asp Thr Ile Val Tyr Ala Tyr Arg Ser Gly Glu Val Ile Arg Leu
615                 620                 625                 630 cca aaa ggg gtt tca att cca gtg aca cta aaa gtt ctg gag ttt gag            2093
Pro Lys Gly Val Ser Ile Pro Val Thr Leu Lys Val Leu Glu Phe Glu
                635                 640                 645 ctt ttc cac ttc tgt cca atc caa gaa ata gct cca agt ata tca ttt            2141
Leu Phe His Phe Cys Pro Ile Gln Glu Ile Ala Pro Ser Ile Ser Phe
        650                 655                 660 gca gca ata ggg cta ctg gat atg ttc aac act gga gga gca gtg gag            2189
Ala Ala Ile Gly Leu Leu Asp Met Phe Asn Thr Gly Gly Ala Val Glu
    665                 670                 675 cag gtt gag att cat aac cga gca gca acg aaa aca ata gct ctt agt            2237
Gln Val Glu Ile His Asn Arg Ala Ala Thr Lys Thr Ile Ala Leu Ser
680                 685                 690 gta agg gga aga ggc aga ttt gga gtt tac tcc tcc cag aga cca ctg            2285
Val Arg Gly Arg Gly Arg Phe Gly Val Tyr Ser Ser Gln Arg Pro Leu
695                 700                 705                 710 aag tgt gtg gta ggt ggc gct gaa acc gac ttc aac tat gac tca gag            2333
Lys Cys Val Val Gly Gly Ala Glu Thr Asp Phe Asn Tyr Asp Ser Glu
                715                 720                 725
```

```
acc ggg ttg aca acc ttc tcc att cca gtt tct cca gag gag atg tac    2381
Thr Gly Leu Thr Thr Phe Ser Ile Pro Val Ser Pro Glu Glu Met Tyr
            730                 735                 740 aga tgg tca ata gag atc caa gtt tgagtccttt ttaagacttg gtgtttgatg   2435
Arg Trp Ser Ile Glu Ile Gln Val
        745                 750 cattgttgta tcaggagaag ggttttgttg taattaagca ttgagggaat tgttggagtc   2495
aggcagagag agagggggga ggtttgttgt aagacaccta gtattagtat catgtagtgg   2555
agaaaaaggg ttgttgatcc taatagctag acaaggcatg ttgtagtagt catgggtgg    2615 ggaagtcctt ttgttgtagc atgtaatttg gtttagactt gtagtatgtc atcaattaga   2675
tggataaaga gagaatattg ttatctaccc gaggatgtaa caatgtttgt ttctctgaat   2735
aaaaagttca catctgtctt ttggaataat aaaaaaaaaa aaaaa                   2780
```

<210> SEQ ID NO 24
<211> LENGTH: 750
<212> TYPE: PRT
<213> ORGANISM: Glycine max cv. Clark63

<400> SEQUENCE: 24

```
Met Thr Val Thr Pro Lys Ile Ser Val Asn Asp Gly Lys Leu Val Val
1               5                   10                  15

His Gly Lys Thr Ile Leu Thr Gly Val Pro Asp Asn Val Val Leu Thr
            20                  25                  30

Pro Gly Ser Gly Arg Gly Leu Val Thr Gly Ala Phe Val Gly Ala Thr
        35                  40                  45

Ala Ser His Ser Lys Ser Leu His Val Phe Pro Met Gly Val Leu Glu
    50                  55                  60

Gly Leu Arg Phe Met Cys Cys Phe Arg Phe Lys Leu Trp Trp Met Thr
65                  70                  75                  80

Gln Arg Met Gly Thr Cys Gly Arg Asp Val Pro Leu Glu Thr Gln Phe
                85                  90                  95

Met Leu Ile Glu Ser Lys Glu Ser Glu Thr Asp Gly Glu Asn Ser Pro
            100                 105                 110

Ile Ile Tyr Thr Val Leu Leu Pro Leu Leu Glu Gly Gln Phe Arg Ala
        115                 120                 125

Val Leu Gln Gly Asn Asp Lys Asn Glu Ile Glu Ile Cys Leu Glu Ser
    130                 135                 140

Gly Asp Asn Ala Val Glu Thr Asp Gln Gly Leu His Met Val Tyr Met
145                 150                 155                 160

His Ala Gly Thr Asn Pro Phe Glu Val Ile Asn Gln Ala Val Lys Ala
                165                 170                 175

Val Glu Lys His Met Gln Thr Phe Leu His Arg Glu Lys Lys Arg Leu
            180                 185                 190

Pro Ser Cys Leu Asp Trp Phe Gly Trp Cys Thr Trp Asp Ala Phe Tyr
        195                 200                 205

Thr Asp Val Thr Ala Glu Gly Val Glu Glu Gly Leu Lys Ser Leu Ser
    210                 215                 220

Gln Gly Gly Thr Pro Pro Arg Phe Leu Ile Ile Asp Asp Gly Trp Gln
225                 230                 235                 240

Gln Ile Glu Asn Lys Ala Lys Asp Ala Thr Glu Cys Leu Val Gln Glu
                245                 250                 255

Gly Ala Gln Phe Ala Thr Arg Leu Thr Gly Ile Lys Glu Asn Thr Lys
            260                 265                 270
```

```
Phe Gln Lys Lys Leu Gln Asn Asn Glu Gln Met Ser Gly Leu Lys His
            275                 280                 285
Leu Val His Gly Ala Lys Gln His His Asn Val Lys Asn Val Tyr Val
        290                 295                 300
Trp His Ala Leu Ala Gly Tyr Trp Gly Val Lys Pro Ala Ala Thr
305                 310                 315                 320
Gly Met Glu His Tyr Asp Thr Ala Leu Ala Tyr Pro Val Gln Ser Pro
                325                 330                 335
Gly Val Leu Gly Asn Gln Pro Asp Ile Val Met Asp Ser Leu Ala Val
            340                 345                 350
His Gly Leu Gly Leu Val His Pro Lys Lys Val Phe Asn Phe Tyr Asn
        355                 360                 365
Glu Leu His Ala Tyr Leu Ala Ser Cys Gly Val Asp Gly Val Lys Val
370                 375                 380
Asp Val Gln Asn Ile Ile Glu Thr Leu Gly Ala Gly His Gly Gly Arg
385                 390                 395                 400
Val Ser Leu Thr Arg Ser Tyr His His Ala Leu Glu Ala Ser Ile Ala
                405                 410                 415
Ser Asn Phe Thr Asp Asn Gly Cys Ile Ala Cys Met Cys His Asn Thr
            420                 425                 430
Asp Gly Leu Tyr Ser Ala Lys Gln Thr Ala Ile Val Arg Ala Ser Asp
        435                 440                 445
Asp Phe Tyr Pro Arg Asp Pro Ala Ser His Thr Ile His Ile Ser Ser
450                 455                 460
Val Ala Tyr Asn Ser Leu Phe Leu Gly Glu Phe Met Gln Pro Asp Trp
465                 470                 475                 480
Asp Met Phe His Ser Leu His Pro Ala Ala Asp Tyr His Ala Ala Ala
                485                 490                 495
Arg Ala Ile Gly Gly Cys Pro Ile Tyr Val Ser Asp Lys Pro Gly Asn
            500                 505                 510
His Asn Phe Asp Leu Leu Lys Lys Leu Val Leu Pro Asp Gly Ser Val
        515                 520                 525
Leu Arg Ala Gln Leu Pro Gly Arg Pro Thr Arg Asp Ser Leu Phe Val
530                 535                 540
Asp Pro Ala Arg Asp Arg Thr Ser Leu Leu Lys Ile Trp Asn Leu Asn
545                 550                 555                 560
Lys Cys Ser Gly Val Val Gly Val Phe Asn Cys Gln Gly Ala Gly Trp
                565                 570                 575
Cys Lys Ile Glu Lys Lys Thr Arg Ile His Asp Thr Ser Pro Gly Thr
            580                 585                 590
Leu Thr Ala Ser Val Cys Ala Ser Asp Val Asp Leu Ile Thr Gln Val
        595                 600                 605
Ala Gly Ala Glu Trp Leu Gly Asp Thr Ile Val Tyr Ala Tyr Arg Ser
610                 615                 620
Gly Glu Val Ile Arg Leu Pro Lys Gly Val Ser Ile Pro Val Thr Leu
625                 630                 635                 640
Lys Val Leu Glu Phe Glu Leu Phe His Phe Cys Pro Ile Gln Glu Ile
                645                 650                 655
Ala Pro Ser Ile Ser Phe Ala Ile Gly Leu Leu Asp Met Phe Asn
            660                 665                 670
Thr Gly Gly Ala Val Glu Gln Val Glu Ile His Asn Arg Ala Ala Thr
        675                 680                 685
Lys Thr Ile Ala Leu Ser Val Arg Gly Arg Gly Arg Phe Gly Val Tyr
```

```
                690             695             700
Ser Ser Gln Arg Pro Leu Lys Cys Val Val Gly Gly Ala Glu Thr Asp
705                 710                 715                 720

Phe Asn Tyr Asp Ser Glu Thr Gly Leu Thr Thr Phe Ser Ile Pro Val
                725                 730                 735

Ser Pro Glu Glu Met Tyr Arg Trp Ser Ile Glu Ile Gln Val
            740                 745                 750

<210> SEQ ID NO 25
<211> LENGTH: 26
<212> TYPE: DNA
<213> ORGANISM: Artificial Sequence
<220> FEATURE:
<223> OTHER INFORMATION: Synthetic DNA

<400> SEQUENCE: 25
atscavcctg actgggatat gttcca                                      26

<210> SEQ ID NO 26
<211> LENGTH: 26
<212> TYPE: DNA
<213> ORGANISM: Artificial Sequence
<220> FEATURE:
<223> OTHER INFORMATION: Synthetic DNA

<400> SEQUENCE: 26
cgaaggayyg awccatcagg aarham                                      26

<210> SEQ ID NO 27
<211> LENGTH: 253
<212> TYPE: DNA
<213> ORGANISM: Arabidopsis thaliana

<400> SEQUENCE: 27
ggcttatgca acctgactgg gaatgttcca tagtctacac ccaactgcag agtaccatgc   60
tgcagcgcgt gcagtgggtg gatgcgcaat ctatgtcagt gataagccag gcaaccacaa  120
ctttgatcta ttgaggaagc tggttcttcc tgatggttca gttcttcggg ctaagctccc  180
gggtaggcct acccgtgact gcttattcgc tgatccagct agagatggga tcagcttgct  240
caagatctgg aac                                                    253

<210> SEQ ID NO 28
<211> LENGTH: 10
<212> TYPE: PRT
<213> ORGANISM: Cucumis sativus

<400> SEQUENCE: 28

Phe Gly Trp Cys Thr Trp Asp Ala Phe Tyr
1               5                   10

<210> SEQ ID NO 29
<211> LENGTH: 13
<212> TYPE: PRT
<213> ORGANISM: Cucumis sativus
<220> FEATURE:
<221> NAME/KEY: MISC_FEATURE
<222> LOCATION: (8)..(8)
<223> OTHER INFORMATION: Xaa is Ala or Cys

<400> SEQUENCE: 29

Val Tyr Val Trp His Ala Leu Xaa Gly Tyr Trp Gly Gly
1               5                   10
```

```
<210> SEQ ID NO 30
<211> LENGTH: 15
<212> TYPE: PRT
<213> ORGANISM: Cucumis sativus

<400> SEQUENCE: 30

His Asn Phe Asp Leu Leu Lys Lys Leu Val Leu Pro Asp Gly Ser
1               5                   10                  15
```

SOYBEAN RAFFINOSE SYNTHASE AND A METHOD FOR PRODUCING RAFFINOSE

This application is a Divisional of U.S. application Ser. No. 09/425,055 filed on Oct. 22, 1999, now U.S. Pat. No. 6,891,084, which is a Continuation of International Application PCT/JP97/03879 filed on Oct. 24, 1997, which is a Continuation-in-Part of U.S. application Ser. No. 08/846,234 filed on Apr. 28, 1997, now U.S. Pat. No. 6,166,292.

TECHNICAL FIELD

The present invention relates to a raffinose synthase, a method for raffinose synthesis using the raffinose synthase or a cell-free extract containing the raffinose synthase, a DNA coding for the raffinose synthase, and methods for its in plants. Raffinose is utilized in a variety of fields, as a food material having an activity to proliferate *Bifidobacterium*, or as a pharmaceutical to be used, for example, for solutions of organ preservation.

BACKGROUND ART

Raffinose is one of raffinose family oligosaccharides, in which galactose is connected to glucosyl group of sucrose via α-1,6 linkage. The raffinose family oligosaccharides include, for example, stachyose containing two connected galactose residues, and verbascose containing three connected galactose residues, in addition to raffinose. These oligosaccharides are widely distributed in plants, for example, seeds of various plants such as beans, rapeseed, and cottonseed containing these oligosaccharides as reserve carbohydrates; plants belonging to Cucurbitaceae such as cucumber and melon containing these sugars as translocation sugars; and sugar beet (*Beta vulgaris*) and rosette leaves having acquired cold resistance.

The raffinose family oligosaccharides are biosynthesized as follows.

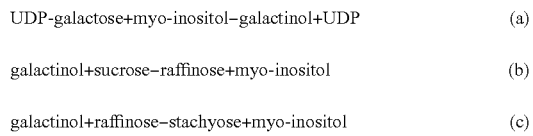

The reactions are catalyzed by (a) galactinol synthase (GS: EC 2.4.1.123), (b) raffinose synthase (RS: EC 2.4.1.82), and (c) stachyose synthase (STS: EC 2.4.1.67), respectively.

At present, raffinose is extracted from sugar beet, and it is separated and purified in the sucrose purification process. However, since crystal formation of sucrose is deteriorated by raffinose, sugar beet has been subjected to breeding and improvement with the aim of decreasing the raffinose content. As a result, the raffinose content in sugar beet now has a low value of 0.03% to 0.16% (*Enzyme Microb. Technol.*, Vol. 4, May, 130-135 (1982)). Therefore, it is not easy to efficiently obtain raffinose from sugar beet having such a low raffinose content.

As described above, raffinose is contained in mature seeds of Leguminosae plants represented by soybean and in sugar beet and Cucurbitaceae plants such as cucumber. Mature seed of soybean contains, as soybean oligosaccharides, sucrose (content: about 5%), stachyose (content: about 4%), and raffinose (content: about 1%). The soybean oligosaccharides are recovered in a fraction obtained by deproteinizing defatted soybean, and they are utilized, for example, for functional food products after concentration. However, raffinose occupies a proportion of 10% of the whole oligosaccharides, and hence raffinose exists in a small amount.

On the other hand, a method for enzymatically synthesizing raffinose has been reported (*Trends in Glycoscience and Glycotechnology*, 7.34, 149-158 (1995)). This method comprises the steps of synthesizing galactobiose in accordance with a condensation reaction catalyzed by α-galactosidase, and transferring galactosyl group to sucrose by using the galactobiose as a galactosyl group donor in accordance with a galactosyl transfer reaction to synthesize raffinose. However, in this reaction, 350 g of galactobiose is synthesized from 1.9 kg of lactose hydrolysate, and 100 g of raffinose is obtained from 190 g of galactobiose and 760 g of sucrose. Therefore, the yield of produced raffinose is low, and hence this synthesis method is not efficient.

Besides the foregoing methods, a method is also conceivable in which a plant having a high raffinose content may be bred by means of transformation for genes for enzymes involved in the biosynthesis system. For example, Kerr et al. have cloned a gene for galactinol synthase, and transformed rapeseed therewith (WO 93/02196). As a result, the GS activity was increased, however, the content of the raffinose family oligosaccharides was unwillingly decreased. It was impossible to achieve the object to enhance the biosynthesis of the raffinose family oligosaccharides by introducing the galactinol synthase gene. Therefore, there has not been provided a method for increasing the content of the raffinose family oligosaccharides in plant.

On the other hand, it is also demanded to decrease the raffinose family oligosaccharides. As described above, the raffinose family oligosaccharides are widely distributed over plants including, seeds of various plants such as beans, for example, soybean, rapeseed, and cottonseed containing these oligosaccharides as storage carbohydrates; Cucurbitaceae plants such as cucumber and melon containing these oligosaccharides as translocation sugars; and sugar beet and rosette leaves having acquired cold resistance. Meals obtained after extraction of oil, for example, from soybean, rapeseed, and cotton contain the raffinose family oligosaccharides. Almost all of the meals are utilized as feed. However, human and animals, which do not have α-galactosidase, cannot directly digest the raffinose family oligosaccharides. It is known that the raffinose family oligosaccharides lower the metabolic energy efficiency of feed due to, for example, assimilation of the raffinose family oligosaccharides by enteric bacteria to cause gas production. It has been reported that removal of raffinose family oligosaccharides from soybean meal results in a large increase in the metabolizable energy for broiler chickens (Coon, "Proceeding Soybean Utilization Alternatives", University of Minnesota, 203-211 (1989)). In view of the foregoing facts, it is desired to develop the plants such as soybean, rapeseed, and cottonseed in which the raffinose family oligosaccharides are decreased.

Such plants have been subjected to breeding to increase the amount of oil. Photosynthetic products are distributed among oils, proteins, and carbohydrates including the raffinose family oligosaccharides. It has been reported for soybean that a reverse correlation exists between the amount of oils and the amount of carbohydrates. It is expected that the content of oils can be increased in a soybean plant having the same photosynthetic ability as those possessed by others, by decreasing the production of the raffinose family oligosaccharides.

Based on a viewpoint as described above, Kerr et al. have reported development of soybean varieties with a low content of the raffinose family oligosaccharides, by means of breeding based on mating and selection, in which the raffinose family oligosaccharides are lowered by an amount of 80% to 90% (WO 93/00742). However, this technique concerns creation of soybean variety, which cannot be applied to other various soybean varieties developed in response to, for example, aptitude for cultivation and resistance to disease. This technique cannot be universally applied to various plants as well.

It is known that raffinose, which is contained, for example, in sugar beet and sugar cane, lowers crystal formation of sugar or sucrose. Therefore, it is possible to expect that if no raffinose is produced, the production efficiency of sugar may be improved in such a plant. However, no sugar beet has been created, which contains no raffinose.

As described above, the raffinose synthase, which has been hitherto purified, has been confirmed only as an enzyme activity, and no entity of the enzyme has been identified. The confirmed activity is low, and it has been desired to obtain a raffinose synthase having a high activity. The conventional method for producing raffinose provides a low yield, and hence it has been desired to develop an efficient method for producing raffinose. On the other hand, it is also desired to breed a plant in which the raffinose family oligosaccharides are decreased.

DISCLOSURE OF THE INVENTION

The present invention has been made taking the foregoing viewpoints into consideration, and an object of the present invention is to obtain a raffinose synthase having a high activity and a DNA encoding the raffinose synthase, and provide an efficient method for enzymatically synthesizing raffinose, and a method for utilizing the DNA encoding the raffinose synthase in plants.

As a result of diligent investigations in order to achieve the object described above, the present inventors have succeeded in purifying a raffinose synthase from cucumber. Further diligent investigations have been made by the present inventors in order to clone a gene coding for the raffinose synthase. As a result, a DNA fragment specific to a gene for the raffinose synthase has been obtained by chemically synthesizing single strand DNAs on the basis of nucleotide sequences deduced from amino acid sequences of peptide fragments of the cucumber raffinose synthase, and performing PCR by using the single strand synthetic DNAs as primers and using cDNAs prepared from poly(A)$^+$RNA extracted from cucumber as templates. Further, the raffinose synthase gene has been isolated by adopting a method in which hybridization is performed for a cDNA library originating from cucumber by using the DNA fragment as a probe. Also, diligent investigations in order to clone a raffinose synthase gene of soybean origin have been made based on information about the raffinose synthase gene of cucumber origin. As a result, the raffinose synthase gene of soybean origin has been isolated. A chimeric gene having a regulatory region expressible in plants has been prepared by using a fragment of the isolated raffinose synthase gene to transform a plant. Further, a plant in which the raffinose family oligosaccharides are decreased due to the introduced raffinose synthase gene, has been created.

Namely, the present invention provides a raffinose synthase having an activity to produce raffinose from sucrose and galactinol.

Preferably, the present invention provides a raffinose synthase which is a protein specified by the following (A), (B), (C) or (D):

(A) a protein which has an amino acid sequence shown in SEQ ID NO: 5 in Sequence Listing;

(B) a protein which comprises an amino acid sequence including substitution, deletion, insertion, addition, or inversion of one or several residues of amino acids in the amino acid sequence shown in SEQ ID NO: 5 in Sequence Listing, and which has an activity to produce raffinose from sucrose and galactinol;

(C) a protein which has an amino acid sequence shown in SEQ ID NO: 24 in Sequence Listing; or (D) a protein which comprises an amino acid sequence including substitution, deletion, insertion, addition, or inversion of one or several residues of amino acids in the amino acid sequence shown in SEQ ID NO: 24 in Sequence Listing, and which has an activity to produce raffinose from sucrose and galactinol.

Also, the present invention provides a raffinose synthase which has the following properties:

(1) action and substrate specificity: produces raffinose from sucrose and galactinol;

(2) optimum pH: about 6 to 8;

(3) optimum temperature: about 35 to 40° C.;

(4) molecular weight:

(i) about 75 kDa to 95 kDa estimated by gel filtration chromatography;

(ii) about 90 kDa to 100 kDa estimated by polyacrylamide gel electrophoresis (Native PAGE); and (iii) about 90 kDa to 100 kDa estimated by SDS-polyacrylamide gel electrophoresis (SDS-PAGE) under a reduced condition; and (5) inhibition: inhibited by iodoacetamide, N-ethylmaleimide, and myo-inositol.

In an embodiment of the foregoing raffinose synthase provided by the present invention, the raffinose synthase has an amino acid sequence including amino acid sequences shown in SEQ ID NOs: 28 to 30 in Sequence Listing.

The present invention also provides a raffinose synthase which is a protein specified by the following (C) or (D):

(C) a protein which has an amino acid sequence shown in SEQ ID NO: 24 in Sequence Listing; or (D) a protein which comprises an amino acid sequence including substitution, deletion, insertion, addition, or inversion of one or several residues of amino acids in the amino acid sequence shown in SEQ ID NO: 24 in Sequence Listing, and which has an activity to produce raffinose from sucrose and galactinol.

In another aspect of the present invention, there is provided a method for producing raffinose, comprising the step of allowing the foregoing raffinose synthase to act on sucrose and galactinol to produce raffinose.

In still another aspect of the present invention, there are provided a DNA encoding the raffinose synthase, and, in particular, a DNA coding for a protein specified by the following (A), (B), (C) or (D):

(A) a protein which has an amino acid sequence shown in SEQ ID NO: 5 in Sequence Listing;

(B) a protein which comprises an amino acid sequence including substitution, deletion, insertion, addition, or inversion of one or several residues of amino acids in the amino acid sequence shown in SEQ ID NO: 5 in Sequence Listing, and which has an activity to produce raffinose from sucrose and galactinol;

(C) a protein which has an amino acid sequence shown in SEQ ID NO: 24 in Sequence Listing; or (D) a protein which comprises an amino acid sequence including substitution, deletion, insertion, addition, or inversion of one or several residues of amino acids in the amino acid sequence shown in SEQ ID NO: 24 in Sequence Listing, and which has an activity to produce raffinose from sucrose and galactinol.

In an embodiment of the foregoing DNA of the present invention, there is provided a DNA specified by the following (a), (b), (c) or (d):

(a) a DNA which includes a nucleotide sequence comprising at least nucleotide residues of nucleotide numbers 56 to 2407 in a nucleotide sequence shown in SEQ ID NO: 4 in Sequence Listing;

(b) a DNA which hybridizes under stringent conditions with the nucleotide sequence comprising at least nucleotide residues of nucleotide numbers 56 to 2407 in the nucleotide sequence shown in SEQ ID NO: 4 in Sequence Listing, and which codes for a protein having an activity to produce raffinose from sucrose and galactinol;

(c) a DNA which includes a nucleotide sequence comprising at least nucleotide residues of nucleotide numbers 156 to 2405 in a nucleotide sequence shown in SEQ ID NO: 23 in Sequence Listing; or (d) a DNA which hybridizes under stringent conditions with the nucleotide sequence comprising at least nucleotide residues of nucleotide numbers 156 to 2405 in the nucleotide sequence shown in SEQ ID NO: 23 in Sequence Listing, and which codes for a protein having an activity to produce raffinose from sucrose and galactinol.

In still another aspect of the present invention, there is provided a DNA useful for expression of an antisense RNA or a sense RNA of the raffinose synthase, namely, a DNA specified by the following (e) or (f):

(e) a DNA which hybridizes under stringent conditions with a nucleotide sequence comprising at least nucleotide residues of nucleotide numbers 56 to 2407 in a nucleotide sequence shown in SEQ ID NO: 4 in Sequence Listing, or a complementary nucleotide sequence thereof; or (f) a DNA which hybridizes under stringent conditions with a nucleotide sequence comprising at least nucleotide residues of nucleotide numbers 156 to 2405 in a nucleotide sequence shown in SEQ ID NO: 23 in Sequence Listing, or a complementary nucleotide sequence thereof.

In still another aspect of the present invention, there are provided a chimeric-gene comprising the raffinose synthase gene or a part thereof, and a transcription regulatory region expressible in plant cells, and a plant transformed with the chimeric gene.

In still another aspect of the present invention, there is provided a method for changing a content of raffinose family oligosaccharides in a plant, comprising the steps of transforming the plant with the chimeric gene, and allowing the gene to be expressed in the plant.

In the following description, the raffinose synthase having the properties described in the foregoing (1) to (5), or the raffinose synthase specified as the protein defined in the foregoing (A), (B), (C) and (D) is simply referred to as "raffinose synthase" in some cases. The DNA encoding raffinose synthase, or the DNA encoding raffinose synthase and including non-translating regions is referred to as "raffinose synthase gene" in some cases.

The present invention will be explained in detail below.

<1> Raffinose Synthase of the Present Invention

The raffinose synthase of the present invention may be a protein specified by the following (A), (B), (C) or (D):

(A) a protein which has an amino acid sequence shown in SEQ ID NO: 5 in Sequence Listing;

(B) a protein which comprises an amino acid sequence including substitution, deletion, insertion, addition, or inversion of one or several residues of amino acids in the amino acid sequence shown in SEQ ID NO: 5 in Sequence Listing, and which has an activity to produce raffinose from sucrose and galactinol;

(C) a protein which has an amino acid sequence shown in SEQ ID NO: 24 in Sequence Listing; or (D) a protein which comprises an amino acid sequence including substitution, deletion, insertion, addition, or inversion of one or several residues of amino acids in the amino acid sequence shown in SEQ ID NO: 24 in Sequence Listing, and which has an activity to produce raffinose from sucrose and galactinol.

The raffinose synthase of the present invention includes that having the following properties:

(1) action and substrate specificity: produces raffinose from sucrose and galactinol;
(2) optimum pH: about 6 to 8;
(3) optimum temperature: about 35 to 40° C.;
(4) molecular weight:
  (i) about 75 kDa to 95 kDa estimated by gel filtration chromatography;
  (ii) about 90 kDa to 100 kDa estimated by polyacrylamide gel electrophoresis (Native PAGE); and
  (iii) about 90 kDa to 100 kDa estimated by SDS-polyacrylamide gel electrophoresis (SDS-PAGE) under a reduced condition; and
(5) inhibition: inhibited by iodoacetamide, N-ethylmaleimide, and myo-inositol.

The raffinose synthase having the foregoing properties has been isolated and purified from leaves of cucumber, and has been identified for the first time by the present inventors. As demonstrated in Examples described later, the raffinose synthase of cucumber origin includes the amino acid residues shown in SEQ ID NOs: 1 to 3 or SEQ ID NOs: 28 to 30 in Sequence Listing, in the amino acid sequence of the enzyme protein. An entire amino acid sequence of the raffinose synthase is shown in SEQ ID NO: 5.

The raffinose synthase is obtainable from plants belonging to Cucurbitaceae, for example, plants such as melon (*Cucumis melo*) and cucumber (*Cucumis sativus*). Especially, the raffinose synthase is contained in a large amount in leaves of these plants, especially in tissues of leaf vein portions and seeds.

Next, the method for producing the raffinose synthase of the present invention will be explained in accordance with an illustrative method for isolating and purifying the raffinose synthase from cucumber.

Leaf vein portions are collected from leaves of cucumber obtained 6 to 10 weeks after planting, and ground with liquid nitrogen by, for example, a mortar. Then, a buffer is added thereto to extract proteins. During this process, it is allowable to add a substance to prevent the raffinose synthase from degradation and inactivation, for example, a protease inhibitor such as PMSF (phenylmethane-sulfonyl fluoride), or polyclarl AT (produced by Serva). Insoluble matters are removed from an obtained extract solution by means of filtration and centrifugation to obtain a crude extract solution.

The crude extract solution thus obtained is subjected to fractionation based on combination of ordinary methods for purifying proteins, including, for example, anion exchange chromatography, hydroxyapatite chromatography, gel filtration, and salting out. Thus the raffinose synthase can be purified.

Anion exchange chromatography can be performed, for example, by using a column charged with a strongly basic anion exchanger such as HiTrap Q (produced by Pharmacia), or a weakly basic anion exchanger such as DEAE-TOYOPE- ARL (produced by Tosoh Corp.). The extract solution containing the raffinose synthase is allowed to pass through the column so that the enzyme is adsorbed to the column. After washing the column, the enzyme is eluted by using a buffer having a high salt concentration. During this process, the salt concentration may be increased in a stepwise manner, or the concentration gradient may be applied. For example, when the HiTrap Q column is used, the raffinose synthase activity adsorbed to the column is eluted by NaCl at about 0.3 M. An eluting solution to give an NaCl concentration gradient of 0.05 M to 0.35 M is preferably used for DEAE-TOYOPE-ARL. An eluting solution to give a phosphate concentration gradient of 0.01 M to 0.3 M is preferably used for hydroxyapatite chromatography.

The order of the foregoing operations is not specifically limited. Each of the operations may be repeated two or more times. It is desirable to exchange a sample solution with an appropriate buffer by means of dialysis or the like before the sample solution is allowed to pass through each column. The sample solution may be concentrated at each stage.

At each stage of the purification, it is preferable that the raffinose synthase activity contained in each of fractionated fractions is measured so that fractions having high activities are collected to be used in the next stage. The method for measuring the raffinose synthase activity is exemplified by a method using radioisotope as reported, for example, by Lehle, H. et al. (*Eur. J. Biochem.*, 38, 103-110 (1973)). As a modified method thereof, the reaction temperature and the substrate concentration may be changed. For example, 10 µl of an enzyme solution is added to a reaction solution containing, at final concentrations, 10 mM $^{14}$C-sucrose, 20 mM galactinol, 25 mM HEPES (2-(4-(2-hydroxyethyl)-1-piperazinyl)ethanesulfonic acid)-NaOH, pH 7.0, 0.5 mM DTT (dithiothreitol) to give a volume of 50 µl. The solution is incubated at 32° C. for 1 hour to perform the reaction. The reaction is stopped by adding 200 µl of ethanol and heating the solution at 95° C. for 30 seconds. The reaction solution is centrifuged to obtain a supernatant. An aliquot of the supernatant is spotted on Whatman 3MM filter paper, and developed with n-propanol:ethyl acetate:water=4:1:2. Incorporation of $^{14}$C into raffinose is investigated, which is regarded to be the raffinose synthase activity (nmol/hour).

The present inventors have developed a method for measuring the raffinose synthase activity in place of the foregoing method. Namely, the raffinose synthase activity is measured by quantitatively determining raffinose produced by the raffinose synthesis reaction, by means of HPLC (high-performance liquid chromatography). According to this method, the activity can be measured conveniently and quickly as compared with the method of Lehle, H. et al. This method is especially preferable to detect active fractions during the purification operation. This method will be explained below.

For the raffinose synthesis reaction, to a reaction solution prepared to have a composition having the following final concentrations, 10 to 50 µl of a raffinose synthase solution is added to give a volume of 100 µl, followed by performing the reaction at 32° C. for 60 minutes.

[Composition of Reaction Solution (Final Concentration)]

| | |
|---|---|
| 2.5 mM | sucrose |
| 5 mM | galactinol |
| 5 mM | DTT |
| 20 mM | Tris-HCl buffer (pH 7.0) |

After performing the reaction as described above, the reaction is stopped by adding to the reaction solution, ethanol in a volume four times the volume of the reaction solution and heating the solution at 95° C. for 30 seconds. The obtained solution is centrifuged to obtain a supernatant and the supernatant is then dried up under a reduced pressure. After that, an obtained residue is dissolved in distilled water. Raffinose in the reaction product is quantitatively determined by using HPLC to estimate the raffinose synthase activity. HPLC can be performed by using, for example, Sugar Analysis System DX500 (CarboPac PA1 column, pulsed amperometry detector (produced by Dionecs)).

FIG. 1 shows a result of measurement performed in accordance with the method described above, for the amount of raffinose produced when the reaction time was changed. As seen from FIG. 1, this method makes it possible to conveniently measure the raffinose synthase activity with excellent linearity.

The degree of purification of the purified raffinose synthase can be confirmed, and the molecular weight can be measured, by means of, for example, gel electrophoresis and gel filtration chromatography. Enzymatic properties can be investigated by measuring the enzyme activity while changing the reaction temperature or the reaction pH, or by measuring the remaining enzyme activity after adding, to the reaction solution, various enzyme inhibitors, metal ions or the like. The stable pH range and the stable temperature range can be investigated by measuring the enzyme activity after exposing the raffinose synthase to various pH conditions and temperature conditions for a certain period of time respectively.

The properties of the raffinose synthase described above have been determined in accordance with procedures as described above. However, it should be noted that different results may be obtained depending on measurement conditions. For example, the measurement for the molecular weight based on the use of gel filtration chromatography is affected by the type of the gel filtration carrier and the buffer, and the molecular weight marker to be used. The enzyme activity differs depending on the type of the buffer and the salt concentration in many cases even when the measurement is performed at an identical pH. Therefore, upon identification for the raffinose synthase, it is preferable to perform comprehensive investigation without being bound to only measurement for individual properties.

The raffinose synthase of the present invention can be obtained by performing the isolation and purification from cucumber as described above. Alternatively, the raffinose synthase of the present invention can be produced by introducing, into an appropriate host, a DNA coding for the raffinose synthase originating from cucumber, soybean or another plant as described later, and making expression thereof, in accordance with ordinary methods used for fermentative production of heterogeneous proteins.

Those assumed as the host for expression of the raffinose synthase gene include various procaryotic cells represented by *Escherichia coli*, and various eucaryotic cells represented by *Saccharomyces cerevisiae*. However, it is desirable to use plant cells, especially cells originating from plants such as tobacco, cucumber, and *Arabidopsis thaliana*.

The recombinant plasmid used for transformation can be prepared by inserting the DNA coding for the raffinose synthase into an expression vector in conformity with the type of cells to be used for expression therein. Those usable as the plant expression vector include those having a promoter DNA sequence operative in the plant or a combination of a plurality of such promoter DNA sequences, and a terminator DNA sequence operative in the plant, and further having a sequence between the both to make it possible to insert a foreign gene.

The promoter includes, for example, promoters which make expression over a whole plant, such as CaMV 35S RNA promoter, CaMV 19S RNA promoter, and nopaline synthase promoter; promoters which make expression in green tissues, such as Rubisco small subunit promoter; and promoters which make site-specific expression at portions such as seed, including, for example, those for genes of napin and phaseolin. The terminator described above includes, for example, nopaline synthase terminator, and Rubisco small subunit 3'-side portion.

As for the expression vector for plants, for example, pBI121 and p35S-GFP (produced by CLONTECH) are commercially available, and they may be used. Alternatively, a vector for expressing virus RNA may be used so that a gene for an outer coat protein encoded thereby, for example, may be replaced with the raffinose synthase gene.

In order to achieve transformation, it is advantageous to use methods which are usually used for transformation, such as the *Agrobacterium* method, the particle gun method, the electroporation method, and the PEG method, in conformity with a host cell to be manipulated. The raffinose synthase activity can be detected by using the method adopted in the purification process for the raffinose synthase. Upon the detection, it is desirable to previously remove α-galactosidase, for example, by allowing the sample to pass through an anion exchange column.

The gene coding for the raffinose synthase of cucumber origin includes all of those which provide the raffinose synthase activity upon expression. Preferably, the gene is exemplified by the gene comprising a DNA coding for the amino acid sequence shown in SEQ ID NO: 5 in Sequence Listing, and the gene having the nucleotide sequence shown in SEQ ID NO: 4 in Sequence Listing. The gene coding for the raffinose synthase of soybean origin includes all of those which provide the raffinose synthase activity upon expression. Preferably, the gene is exemplified by the gene comprising a DNA coding for the amino acid sequence shown in SEQ ID NO: 24 in Sequence Listing, and the gene having the nucleotide sequence shown in SEQ ID NO: 23 in Sequence Listing. It is noted that the gene coding for the amino acid sequence shown in SEQ ID NO: 5 or 24 in Sequence Listing includes various nucleotide sequences taking degeneracy of codons into consideration. Namely, the gene coding for the amino acid sequence shown in SEQ ID NO: 5 or 24 in Sequence Listing may be selected from such various nucleotide sequences, while considering several factors for the gene expression system, such as preferential codons depending on, for example, the type of the host cell, and avoidance of higher-order structure to be formed by transcribed RNA. The selected nucleotide sequence may be a DNA cloned from the nature, or a DNA chemically synthesized in an artificial manner.

<2> DNA Coding for Raffinose Synthase of the Present Invention

The DNA coding for the raffinose synthase can be obtained by preparing a cDNA library from poly(A)$^+$RNA isolated from a plant such as cucumber, and screening the cDNA library by means of hybridization. A probe to be used for the hybridization can be obtained by performing amplification by means of PCR (polymerase chain reaction) by using, as primers, oligonucleotides synthesized on the basis of partial amino acid sequences of the raffinose synthase protein.

A method for obtaining the DNA of the present invention from poly(A)$^+$RNA originating from cucumber will be specifically explained below.

As for the portion for extracting poly(A)$^+$RNA, all portions of a cucumber plant body may be used provided that the raffinose synthase gene is expressed at that portion. Poly(A)$^+$RNA can be obtained, for example, from leaves, stalks, buds, fruits, and seeds at various growth stages. However, poly(A)$^+$RNA is desirably obtained from a material of fully expanded leaves after fruiting, especially leaf vein portions.

In order to extract total RNA from the cucumber tissue, any method may be used without limitation provided that RNA can be efficiently obtained with less damage. It is possible to use any known method such as the phenol/SDS method and the guanidine isothiocyanate/cesium chloride method. Poly (A)$^+$RNA can be isolated from the total RNA thus obtained, by using an oligo(dT) carrier. It is also preferable to use a kit (for example, MPG Direct mRNA Purification Kit, produced by CPG, INC.) which makes it possible to obtain poly(A)$^+$RNA without extracting the total RNA.

A DNA fragment, which is used as a probe for screening for the cDNA library, can be obtained by performing PCR. Oligonucleotides, which have nucleotide sequences deduced from already known amino acid sequences of peptide fragments, for example, nucleotide sequences deduced from amino acid sequences shown in SEQ ID NOs: 1 to 3, are chemically synthesized. The obtained oligonucleotides are used as primers to perform PCR. Any portion of the amino acid sequence of the obtained peptide fragment may be used for the primers. However, it is desirable to select sequences which include less degeneracy of codons and which are assumed to form no complicated higher-order structure. Alternatively, it is also preferable to perform RACE (Rapid Amplification of cDNA End, "PCR PROTOCOLS A Guide to Methods and Applications", ACADEMIC press INC., pp. 28 to 38).

It is desirable to use, as a template for PCR, a cDNA library or single strand cDNA. When a heat-resistant DNA polymerase having a reverse transcriptase activity is used for the PCR reaction, it is allowable to use poly(A)$^+$RNA, or total RNA in some cases.

In order to prepare the cDNA library, at first single strand cDNAs are synthesized by using reverse transcriptase while using poly(A)$^+$RNA as a template and using oligo(dT) primer, random primers or the like. Next, double strand cDNAs are synthesized in accordance with, for example, the Gubler and Hoffman method, the Okayama-Berg method ("Molecular Cloning", 2nd edition, Cold Spring Harbor press, 1989). When the raffinose synthase gene is expressed in a small amount, cDNAs may be amplified by means of PCR by using a cDNA library construction kit using PCR (for example, Capfinder PCR cDNA Library Construction Kit (produced by CLONTECH)). cDNAs thus synthesized can be cloned into a cloning vector such as phage vectors and plasmids, after performing, for example, blunt end formation, addition of a linker, addition of a restriction enzyme site by means of PCR.

A portion characteristic of the raffinose synthase cDNA is selected from the DNA fragments obtained by PCR described above, for the probe for hybridization. It is desirable to select a DNA fragment located near to the 5'-terminal side. The amplified DNA fragment thus selected is purified from a reaction solution of PCR. In this procedure, the amplified DNA fragment may be purified by subcloning the DNA fragment by using a plasmid, preparing a large amount of the subcloned plasmid, digesting the prepared plasmid with a restriction enzyme, and excising the DNA fragment from a gel after electrophoresis. Alternatively, PCR may be performed by using the plasmid as a template to amplify and use only the objective portion. When the amount of the initially amplified DNA fragment is sufficiently large, the amplified DNA fragment may be purified by electrophoresing the DNA fragment without performing subcloning, excising a gel segment containing a band of the objective DNA fragment, and purifying the DNA fragment from the gel segment.

Screening to obtain the objective clone from the cDNA library is performed by means of hybridization. The DNA fragment obtained in accordance with the foregoing method can be labeled and used as a probe for the hybridization. Upon labeling, it is possible to use various labels such as radioisotope and biotin. However, labeling is desirably performed in accordance with the random priming method. Screening may be performed by using PCR instead of hybridization. Further, screening may be performed by using hybridization and PCR in combination.

The nucleotide sequence of the DNA coding for the raffinose synthase of cucumber origin obtained as described above, and the amino acid sequence deduced from the nucleotide sequence are illustratively shown in SEQ ID NO: 4 in Sequence Listing. Only the amino acid sequence is shown in SEQ ID NO: 5. A transformant AJ13263 of *Escherichia coli* JM109, which harbors a plasmid pMossloxCRS containing the DNA fragment including the DNA coding for the raffinose synthase obtained in Example 3 described later, has been internationally deposited on the basis of the Budapest Treaty since Nov. 19, 1996 in National Institute of Bioscience and Human Technology of Agency of Industrial Science and Technology of Ministry of International Trade and Industry (postal code: 305, 1-3 Higashi 1-chome, Tsukuba-shi, Ibaraki-ken, Japan), and awarded an accession number of FERM BP-5748.

Furthermore, by using the raffinose synthase gene obtained from one plant as described above, a raffinose synthase gene can be obtained from another plant. As the plant for obtaining the raffinose synthase, any of plants producing raffinose as described above may be used. For example, soybean, broad bean, rapeseed, sunflower, cotton, sugar beet and the like may be mentioned. As an example, acquisition of the DNA encoding the raffinose synthase gene of soybean by using the DNA encoding the raffinose synthase gene of cucumber origin is described.

The raffinose synthase gene of soybean can be obtained by preparing a cDNA library from poly(A)⁺RNA derived from soybean, and screening the cDNA library by using a probe selected based on the nucleotide sequence of the DNA encoding the raffinose synthase gene of cucumber origin.

As a portion from which RNA is extracted, any portion of soybean plant body can be used provided that the raffinose synthase is expressed. Preferably, a seed, in particular, an immature seed after bloom which produces raffinose family oligosaccharides, may be used.

The method for extracting total RNA from the soybean immature seed is not limited provided that less-damaged. RNA can be efficiently obtained. Any of the methods described above with respect to cucumber may be used.

A probe for hybridization needs to have a nucleotide sequence having a high homology with the raffinose synthase gene of soybean origin. The probe used for hybridization may be the raffinose synthase gene of cucumber origin. Preferably, a sequence of a region conserved in the raffinose synthase in the gene may be used as a probe. However, the sequence can not be determined based on only information about the raffinose synthase gene of cucumber origin. To obtain the probe for hybridization having the sequence, the following methods needs to be used. Conveniently, Northern hybridization to soybean RNA is carried out with fragments obtained by digesting the raffinose synthase gene of cucumber origin with a suitable restriction enzyme, and a DNA fragment which hybridizes may be used as the probe. Alternatively, the probe may be obtained by RT-PCR using primers synthesized based on an amino acid sequence of the raffinose synthase of cucumber origin and soybean RNA as a template. Also, the probe may be obtained by RT-PCR using oligonucleotides synthesized based on *Arabidopsis thaliana* EST sequences having homology with the DNA encoding the raffinose synthase of cucumber origin as primers and *Alabidopsis thaliana* RNA.

Preferably, one having a high homology with the objective gene is obtained as follows. First, EST sequences of *Arabidopsis thaliana* or the like which has homology with the raffinose synthase gene of cucumber origin in GenBank are screened with software such as Genetix Mac or the like. Regions of a high homology between the obtained sequences and the raffinose synthase gene of cucumber are considered to include a region conserved among raffinose synthases originating from various species. A DNA fragment of this region can be obtained by, for example, amplification by PCR using single strand DNA prepared from *Arabidopsis thaliana* RNA as a template and oligonucleotides synthesized based on the sequence of a high homology as primers. The nucleotide sequence of the amplified fragment is analyzed to select one having a sequence of a high homology with that of cucumber. The obtained DNA fragment is labeled as described above to use as the probe.

For screening of the objective clone from a cDNA library, hybridization may be carried out in the same manner as cloning the gene of cucumber.

A nucleotide sequence of a DNA encoding the raffinose synthase of soybean origin obtained as described above, and an amino acid sequence deduced from the nucleotide sequence are shown in SEQ ID NO: 23 in Sequence Listing. Only the amino acid sequence is shown in SEQ ID NO: 24. Homology of the raffinose synthase of soybean origin with the raffinose synthase of cucumber origin is 38% in the amino acid sequence and 50% in the nucleotide sequence by maximum matching which allows gaps. The transformant, designated as AJ13379, of *Escherichia coli* JM109, which harbors the plasmid pMOSSloxSRS containing a DNA fragment containing DNA coding for the raffinose synthase obtained in Example 4 as described below, has been internationally deposited on the basis of the Budapest Treaty since Oct. 20, 1997 in National Institute of Bioscience and Human Technology of Agency of Industrial Science and Technology of Ministry of International Trade and Industry (postal code: 305, 1-3 Higashi 1-chome, Tsukuba-shi, Ibaraki-ken, Japan), and awarded an accession number of FERM BP-6149.

By using information about the raffinose synthase of cucumber origin and the raffinose synthase of soybean origin, a raffinose synthase gene may be obtained from another plant. Single strand DNA having a nucleotide sequence deduced from the amino acid sequence conserved between the both proteins, for example, SEQ ID NO: 28 (amino acid numbers 199 to 208 of SEQ ID NO: 24), 29 (amino acid numbers 302 to 314 of SEQ ID NO: 24), 30 (amino acid numbers 513 to 527 of SEQ ID NO: 24) in Sequence Listing, or single strand DNA having a nucleotide sequence complementary to the deduced nucleotide sequence may be synthesized and RT-PCR may be carried out by using the single strand DNAs as primers. Any portion of the sequence may be used for the primer. Preferably, a sequence in which degeneracy of codon is small and complicated high-order structure is not considered to be formed. PCR is carried out by using cDNA synthesized from total RNA or poly(A)+RNA in some cases of a plant from which the gene is to be obtained, as a template. The obtained DNA fragment is cloned into a suitable vector to analyze nucleotide sequence, thereby confirming that the nucleotide sequence has homology with the raffinose synthase gene originating from cucumber or soybean or an amino acid sequence translated therefrom has homology with the amino acid sequence of the raffinose synthase originating from cucumber or soybean. Thus obtained DNA fragment can be used for screening of a cDNA library. Alternatively, RACE may be carried out using single strand cDNA synthesized from total RNA or poly(A)+RNA in some cases of a plant from which the gene is to be obtained, as a template.

The DNA of the present invention may code for a raffinose synthase protein including substitution, deletion, insertion, addition, or inversion of one or several residues of amino acids at one or several positions, provided that the activity of raffinose synthase encoded thereby, i.e., the activity to produce raffinose from sucrose and galactinol is not deteriorated. In this context, the number of "several residues" differs depending on the position and the type of the amino acid residues in the three-dimensional dimensional structure of the protein, originally because of the following reason. Namely, high similarity is found between some amino acids and other amino acids, for example, between isoleucine and valine, and such a difference in amino acid does not greatly affect the three-dimensional structure of the protein. Therefore, the DNA of the present invention may code for those having homology of not less than 35 to 40% with respect to the entire 784 amino acid residues for constituting the raffinose synthase of cucumber origin, provided that they have the raffinose synthase activity. Preferably, they have homology of 65% in a region between 510th amino acid and 610th amino acid. Also, the DNA of the present invention may code for those having homology of not less than 35 to 40% with respect to the entire 750 amino acid residues for constituting the raffinose synthase of soybean origin, provided that they have the raffinose synthase activity. Preferably, they have homology of 65% in a region between 478th amino acid and 577th amino acid. Specifically, the number of "several residues" is 2 to 40, preferably 2 to 20, and more preferably 2 to 10. The homology is a value determined by the maximum matching which allows gaps.

The present invention includes genes in which homology of not less than about 50% is given for the entire length of the gene, and homology of not less than 65% is given over a region comprising about 300 nucleotide residues. Nucleotide sequence information on such genes can be obtained by searching genes having homology to the raffinose synthase gene of cucumber origin, by using a database such as GenBank. For example, GENETIX-MAC (software for processing genetic information, produced by Software Development), which adopts the Lipman-Person method, may be used as a program for homology analysis. Alternatively, those open to the public on the Internet may be used for this purpose. Some nucleotides sequences obtained by the method as described above contain the entire length of the gene, and other nucleotide sequences do not contain the entire length of the gene. When the entire length of the gene is not contained, the entire length gene can be easily obtained by using RNA extracted from an objective plant tissue as a template, and using primers corresponding to portions having high homology to the raffinose synthase gene of cucumber origin, in accordance with the 5'-RACE method and the 3'-RACE method. The obtained entire length gene may be incorporated into an appropriate expression vector provided as those included in a kit such as Soluble Protein Expression System (produced by INVITROGEN), Tight Control Expression System (produced by INVITROGEN), and QIAexpress System (produced by QIAGEN) as described above, so that the gene may be expressed, and then the raffinose synthase activity may be measured in accordance with the method described above to select a clone having the activity. The methods for gene expression are detailed in Plant Molecular Biology, A Laboratory Manual (Melody S. Clark (Ed.), Springer) and the like.

A DNA, which codes for substantially the same protein as the raffinose synthase, can be obtained by modifying the nucleotide sequence in accordance with, for example, the site-directed mutagenesis method so that amino acids located at specified positions are subjected to substitution, deletion, insertion, or addition. The modified DNA as described above may be also obtained in accordance with the conventionally known mutation treatment. The mutation treatment includes a method in which the DNA coding for the raffinose synthase is treated with hydroxylamine or the like in vitro, and a method in which a bacterium belonging to the genus *Escherichia* harboring the DNA coding for the raffinose synthase is treated with ultraviolet irradiation or a mutating agent usually used for artificial mutation, such as nitrous acid and N-methyl-N'-nitro-N-nitrosoguanidine (NTG).

The substitution, deletion, insertion, addition, or inversion of the nucleotide includes mutation which naturally occurs, for example, based on the difference between individuals of a cucumber or soybean plant, the difference between varieties, the formation of multiple copies of the gene, the difference between respective organs, and the difference between respective tissues.

DNA having mutation as described above is expressed in an appropriate cell to investigate the raffinose synthase activity of an expressed product. Thus it is possible to obtain a DNA which codes for substantially the same protein as the raffinose synthase. Further, the DNA coding for substantially the same protein as the raffinose synthase protein can be obtained by isolating a DNA which hybridizes under stringent conditions with a DNA having a nucleotide sequence comprising nucleotide residues of nucleotide numbers 56 to 2407 in the nucleotide sequence shown in SEQ ID NO: 4 or a nucleotide sequence comprising nucleotide residues of nucleotide numbers 156 to 2405 in the nucleotide sequence shown in SEQ ID NO: 23 in Sequence Listing, for example, and which codes for the protein having the raffinose synthase activity, from DNAs coding for raffinose synthases having mutation or from cells harboring the DNAs. The phrase "stringent conditions" referred to herein indicates a condition in which the specific hybrid is formed, and nonspecific hybrid is not formed. It is difficult to definitely express this condition by using numerical values. However, for example, this condition includes a condition in which DNAs having high homology, for example, DNAs having homology of not less than 50% hybridize with each other, while DNAs having homology lower than the above do not hybridize with each other, or a condition in which hybridization is achieved at a salt concentration corresponding to a washing condition for ordinary Southern hybridization, i.e., 1×SSC, 0.1% SDS, and preferably 0.1×SSC, 0.1% SDS, at 60° C. Genes, which hybridize under such a condition, may include those which contain a stop codon generated at an intermediate position, and those which have lost the activity due to mutation at the active center. However, those having such mutation can be easily eliminated by ligating the gene with a commercially available activity expression vector to measure the raffinose synthase activity in accordance with the method described above.

When the DNA of the present invention is used to express an antisense RNA for the raffinose synthase, it is unnecessary for the DNA to code for any active raffinose synthase. Further, the function of any endogenous gene having homology can be restrained by using a sense RNA. In such a case, it is also unnecessary for the DNA to code for any active raffinose synthase. Further, it is unnecessary for the DNA to contain the entire length. Preferably, it is sufficient for the DNA to have about 500 base pairs of a translating region having 60% of homology. An example of the DNA is a DNA of the following (e) or (f):

(e) a DNA which hybridizes under stringent conditions with a nucleotide sequence comprising at least nucleotide residues of nucleotide numbers 56 to 2407 in a nucleotide sequence shown in SEQ ID NO: 4 in Sequence Listing, or a complementary nucleotide sequence thereof; or (f) a DNA which hybridizes under stringent conditions with a nucleotide sequence comprising at least nucleotide residues of nucleotide numbers 156 to 2405 in a nucleotide sequence shown in SEQ ID NO: 23 in Sequence Listing, or a complementary nucleotide sequence thereof.

The method has been explained above, in accordance with which the present inventors have succeeded in cloning the objective cDNA of the raffinose synthase originating from cucumber or soybean. However, other than the foregoing, the following methods may be available.

(1) The raffinose synthase originating from cucumber or soybean is isolated and purified, and an entire nucleotide sequence is chemically synthesized on the basis of a determined amino acid sequence or the amino acid sequence shown in SEQ ID NO: 5 or 24.

(2) Chromosomal DNA is prepared from a cucumber or soybean plant body, and a chromosomal DNA library is prepared by using a plasmid vector or the like. The raffinose synthase gene is obtained from the library by means of hybridization or PCR. It is assumed that the raffinose synthase gene originating from chromosome contains intron in its coding region. However, DNA divided into several parts by such intron is included in the DNA of the present invention provided that it codes for the raffinose synthase.

(3) Poly(A)+RNA is fractionated into fractions in accordance with the molecular weight or the like. The fractions are subjected to an in vitro translation system using wheat germ or rabbit reticulocyte to determine a fraction containing mRNA coding for a polypeptide having the raffinose synthase activity. An objective cDNA fragment is prepared and obtained from the fraction.

(4) An anti-cucumber raffinose synthase antibody or an anti-soybean raffinose synthase antibody is prepared. Elements of a cDNA library are incorporated into a protein expression vector, and an appropriate host is transfected therewith to express proteins encoded by cDNAs. An objective cDNA may be screened by using the foregoing antibody.

(5) Appropriate primers are synthesized on the basis of amino acid sequences of peptide fragments, and a sequence containing the terminal is amplified by means of the RACE method, followed by cloning thereof.

For expression of the raffinose synthase gene, a DNA of a region encoding the enzyme may be introduced to various expression vectors to express the gene. Specifically, it is described in Plant Molecular Biology-A Laboratory Manual (M. S. Clark (eds.), Springer) and the like. As the vector, commercially available expression vectors may be used. Confirmation of the expression can be carried out by measuring an activity according to the method described in the present specification.

As an example, a method for expression of the raffinose synthase activity by the raffinose synthase gene originating from soybean is described. An NdeI restriction enzyme site and a BamHI site are added to immediately upstream portion including ATG of 156th nucleotide and downstream portion of 2405th nucleotide, respectively, by PCR using primers designed to have the respective restriction enzyme sites. Then, the raffinose synthase gene purified by the phenol-chloroform method and pET3a are each digested with NdeI and BamHI. The digested DNAs are each purified by agarose gel electrophoresis. Since a BamHI site is present in the raffinose synthase gene originating from soybean, mutation is previously made by PCR or the like, or a fragment having an objective size is selected by agarose gel electrophoresis. The purified raffinose synthase gene fragment is ligated to the vector, and the ligation is confirmed by agarose gel electrophoresis. Also, sequencing is carried out to confirm that the raffinose synthase gene starts from ATG codon. *E. coli* BL21 (DE3) pLysE is transformed with the vector, and transformants are selected with LB medium containing chloramphenicol and ampicillin. The insert fragment in the transformant is confirmed by PCR or the like, the objective transformant is cultured to obtain cells. The cells are incubated with a gel-loading buffer containing SDS at 100° C. for 3 minutes. Then, SDS polyacrylamide gel electrophoresis is carried out to confirm a protein band of an objective size. The selected strain is cultured, and protein is extracted by disrupting cells with sonication or the like. The raffinose synthase activity of the extracted protein solution may be determined by the method described in the present specification.

<3> Method for Producing Raffinose of the Present Invention

In the method for producing raffinose of the present invention, the raffinose synthase is allowed to act on sucrose and galactinol to produce raffinose. When the raffinose synthase is allowed to act on sucrose and galactinol, the galactose residue constituting galactinol is transferred to sucrose, and thus raffinose is produced. During this process, myo-inositol constituting galactinol is liberated.

The raffinose synthase, which is used to produce raffinose, may be an enzyme extracted from a plant body, or an enzyme produced by means of the genetic recombination technique based on the use of the DNA of the present invention.

In order to allow the raffinose synthase to act on sucrose and galactinol, the following procedure may be available. Namely, the raffinose synthase or cells having an ability to produce the raffinose synthase are immobilized to a carrier such as alginic acid gel and polyacrylamide gel to prepare immobilized enzyme or immobilized cells. The immobilized enzyme or the immobilized cells are charged to a column, and a solution containing sucrose and galactinol is allowed to pass through the column. As for the carrier and the method for immobilizing the raffinose synthase or the cells to the carrier, it is possible to adopt materials and methods which are used for ordinary bioreactors.

The raffinose synthesis reaction is performed, for example, by adding the raffinose synthase to a solution such as an aqueous solution or a buffer containing sucrose and galactinol. It is preferable that pH of the solution is adjusted to be within a range of about 6 to 8, especially at about pH 7. The reaction temperature is within a range of about 28 to 42° C., preferably 35 to 40° C., especially about 38° C. The raffinose synthase of the present invention is stable within a range of pH 5 to 8, especially in the vicinity of pH 6. The enzyme of the present invention is stable within a temperature range of not more than about 40° C.

The enzyme activity of the raffinose synthase of the present invention is inhibited by iodoacetamide, N-ethylmaleimide, $MnCl_2$, $ZnCl_2$, and $NiCl_2$. Therefore, it is desirable that these substances are not contained in the reaction solution.

Preferably, galactinol and sucrose are added to the reaction solution at a concentration of not less than 5 mM of galactinol and a concentration of not less than 1.5 mM of sucrose. The raffinose synthase may be added to the reaction solution in an amount depending on the amounts of the substrates.

Raffinose is separated from unreacted sucrose and galactinol and from myo-inositol produced by the enzyme reaction, contained in the reaction solution, in accordance with a method including, for example, gel filtration chromatography.

<4> Chimeric Gene and Transgenic Plant of the Present Invention

The chimeric gene of the present invention includes the raffinose synthase gene or a part thereof and the transcription regulatory region expressible in plant cells. The raffinose synthase gene is exemplified by the DNA coding for the raffinose synthase of the present invention described in the foregoing item <2>. When the chimeric gene of the present invention is used as an antisense gene, a non-coding region of the raffinose synthase gene or a part thereof can be used in some cases, besides the DNA coding for the raffinose synthase. The non-coding region includes, for example, sequences indicated by nucleotide numbers 1 to 55 (5'-non-coding region) and nucleotide numbers 2407 to 2517 (3'-non-coding region) in SEQ ID NO: 4 as well as nucleotide numbers 1 to 155 and nucleotide numbers 2406 to 2765 in SEQ ID NO: 23 in Sequence Listing.

When the transcription regulatory region is linked to the DNA coding for the raffinose synthase in the chimeric gene of the present invention so that mRNA (sense RNA) homologous to the coding strand of the DNA is expressed, plant cells to which the chimeric gene is introduced express the raffinose synthase, and the content of the raffinose family oligosaccharides is increased. On the other hand, when the transcriptional regulatory region is linked to the DNA so that RNA (antisense RNA) having a sequence complementary to the coding strand of the DNA is expressed, and when the transcription regulatory region is linked to the DNA so that a partial fragment of the raffinose synthase gene, preferably sense RNA for a portion of not less than about 200 base pairs in the upstream coding region is expressed, then the expression of endogenous raffinose synthase is restrained in plant cells to which the chimeric gene is introduced, and the raffinose family oligosaccharides are decreased.

The content of the raffinose family oligosaccharides in a plant can be changed by transforming the plant with the chimeric gene of the present invention, and allowing the gene to be expressed in cells of the plant.

Plants to which the present invention is applicable include, for example, oil crops such as soybean, rapeseed, cotton; sugar crops such as sugar beet and sugar cane; and model plants represented by *Arabidopsis thaliana*.

The transcription regulatory region expressible in plant cells includes, for example, promoters which make expression over a whole plant, such as CaMV 35S RNA promoter, CaMV 19S RNA promoter, and nopaline synthase promoter; promoters which make expression in green tissues, such as Rubisco small subunit promoter; and promoter regions which make site-specific expression at portions such as seed, including, for example, those for genes of napin and phaseolin as described above. The 3'-terminal of the chimeric gene may be connected with the terminator such as nopaline synthase terminator, and Rubisco small subunit 3'-end portion.

The plant may be transformed with the chimeric gene in accordance with usually used methods such as the *Agrobacterium* method, the particle gun method, the electroporation method, and the PEG method, depending on the host cell to be manipulated.

The transformation method for introducing the chimeric gene into the plant includes, for example, the *Agrobacterium* method, the particle gun method, the electroporation method, and the PEG method.

The *Agrobacterium* method is specifically exemplified by a method using a binary vector. Namely, a plant is transfected with a vector comprising T-DNA originating from Ti plasmid, a replication origin which is functional in microorganisms such as *Escherichia coli*, and a marker gene for selecting plant cells or microbial cells harboring the vector. Seeds are collected from the plant, and they are allowed to grow. Plants to which the vector is introduced are selected by using an index of expression of the marker gene. Obtained plants are measured for the raffinose synthase activity, or strains exhibiting change in content of the raffinose family oligosaccharides are selected from the obtained plants. Thus it is possible to obtain an objective transformed plant.

A method for introducing the chimeric gene into soybean will be described below. In order to perform transformation for soybean, it is possible to use any of the particle gun method (*Pro. Natl. Acad. Sci. USA*, 86, 145 (1989); *TIBTECH*, 8, 145 (1990); *Bio/Technology*, 6, 923 (1988); *Plant Physiol*, 87, 671 (1988); *Develop. Genetics*, 11, 289 (1990); and *Plant cell Tissue & Organ Culture*, 33, 227 (1993)), the *Agrobacterium* method (*Plant Physiol.*, 91, 1212 (1989); WO 94/02620; *Plant Mol. Biol.*, 9, 135 (1987); and *Bio/Technology*, 6, 915 (1988)), and the electroporation method (*Plant Physiol*, 99, 81 (1992); *Plant Physiol*, 84, 856 (1989); and *Plant Cell Reports*, 10, 97 (1991)).

In the particle gun method, it is preferable to use an embryogenic tissue or a hypocotyl of an immature seed about 30 to 40 days after dehiscence of anthesis. About 1 g of the embryogenic tissue is spread over a petri dish, and, for example, gold particles or tungsten particles coated with the objective chimeric gene may be shot thereinto. The tissue is transferred after 1 to 2 hours to a liquid medium to perform cultivation. After 2 weeks, the tissue is transferred to a medium containing an antibiotic for transformant selection, followed by cultivation. After 6 weeks, a green adventitious embryo which is resistant to the antibiotic is obtained. The adventitious embryo is further transferred to a fresh medium and cultured so that a plant body is reproduced. Alternatively, when the hypocotyl is used, the hypocotyl is excised under a sterilized condition, and it is treated in accordance with the particle gun method, followed by cultivation in MS medium (Murashige and Skoog, *Physiologia Plantrum*, 15, 473-497 (1962)) containing cytokinin at a high concentration. The hypocotyl is cultured in the darkness for 2 weeks, and then it is cultured at room temperature with light irradiation for 12 to 16 hours in MS medium having a lowered cytokinin content. During this process, it is preferable to add, to the medium, the antibiotic having been used as the selection marker. When a multiple bud body is formed from the transplanted tissue, it is transferred to a medium supplemented with no hormone so that rooting is caused. An obtained seedling body is transferred to a greenhouse and cultivated.

In the case of the method using *Agrobacterium*, it is desirable to use cotyldonary nod as a plant tissue. Commercially available LBA4404, C58, and Z707 can be used as *Agrobacterium*. It is desirable to use Z707. For example, a plasmid obtained by inserting the objective gene into pMON530 (produced by Monsanto Co.) can be used as the vector. The plasmid is introduced into *Agrobacterium tumefaciens* Z707 (Hepburn et al., *J. Gen. Microbiol.*, 131, 2961 (1985)) in accordance with, for example, the direct freeze thaw method (An et al., "Plant Mol. Biol. Mannual", A3: 1-19, 1988). The *Agrobacterium* transformed with the chimeric gene is cultivated overnight. Proliferated cells are collected by centrifugation at 5000 rpm for 5 minutes, and they are suspended in B5 suspension medium. Soybean seeds are sterilized, and they are cultivated for 3 days on B5 medium having a 1/10 concentration so that they germinate. Cotyledons are excised, and they are cultivated for 2 hours with the suspension of *Agrobacterium*. The cotyledons are transferred to B5 medium (containing Gamborg B5 salt (*Exp. Cell. Res.*, 50, 151 (1968)), Gamborg B5 vitamin, 3% sucrose, 5 µM benzylaminopurine, 10 µM IBA, and 100 µM acetosyringon), and they are cultivated for 3 days under a condition at 25° C. with light irradiation (60 µEm$^{-2}$S$^{-1}$) for 23 hours. Subsequently, in order to remove *Agrobacterium*, the cotyledons are cultivated in B5 medium (5 µM benzylaminopurine, 100 mg/L carbenicillin, 100 mg/L vancomycin, and 500 mg/L cefotaxime) at 25° C. for 4 days while exchanging the medium every day. After that, the cotyledons are cultivated in B5 medium (200 mg/L kanamycin). Multishoots are formed within 1 or 2 months. They are cultivated on B5 medium (0.58 mg/L gibberellin and 50 mg/L kanamycin) to elongate the shoots. Subsequently, the shoots are transferred to B5 medium (10 µM IBA) to cause rooting. Rooted seedlings are acclimatized, and they are cultivated in a greenhouse. Thus transformants can be obtained.

A transformant plant, in which the raffinose synthase gene is introduced, can be easily confirmed by extracting DNA from the transformant, and performing Southern hybridization by using the raffinose synthase gene as a probe.

BRIEF DESCRIPTION OF THE DRAWINGS

FIG. 2 shows a diagram illustrating a result of SDS-polyacrylamide gel electrophoresis for the raffinose synthase. M indicates molecular weight markers, and S indicates a sample containing the raffinose synthase. Numerals indicate molecular weights (kDa).

FIG. 7 shows relationships between synthetic primers and amino acid sequences of peptides. R represents A or G, Y represents C or T, M represents A or C, K represents G or T, D represents G, A, or T, H represents A, T, or C, B represents G, T, or C, N represents G, A, T, or C, and I represents inosine.

BEST MODE FOR CARRYING OUT THE INVENTION

Figure 1:
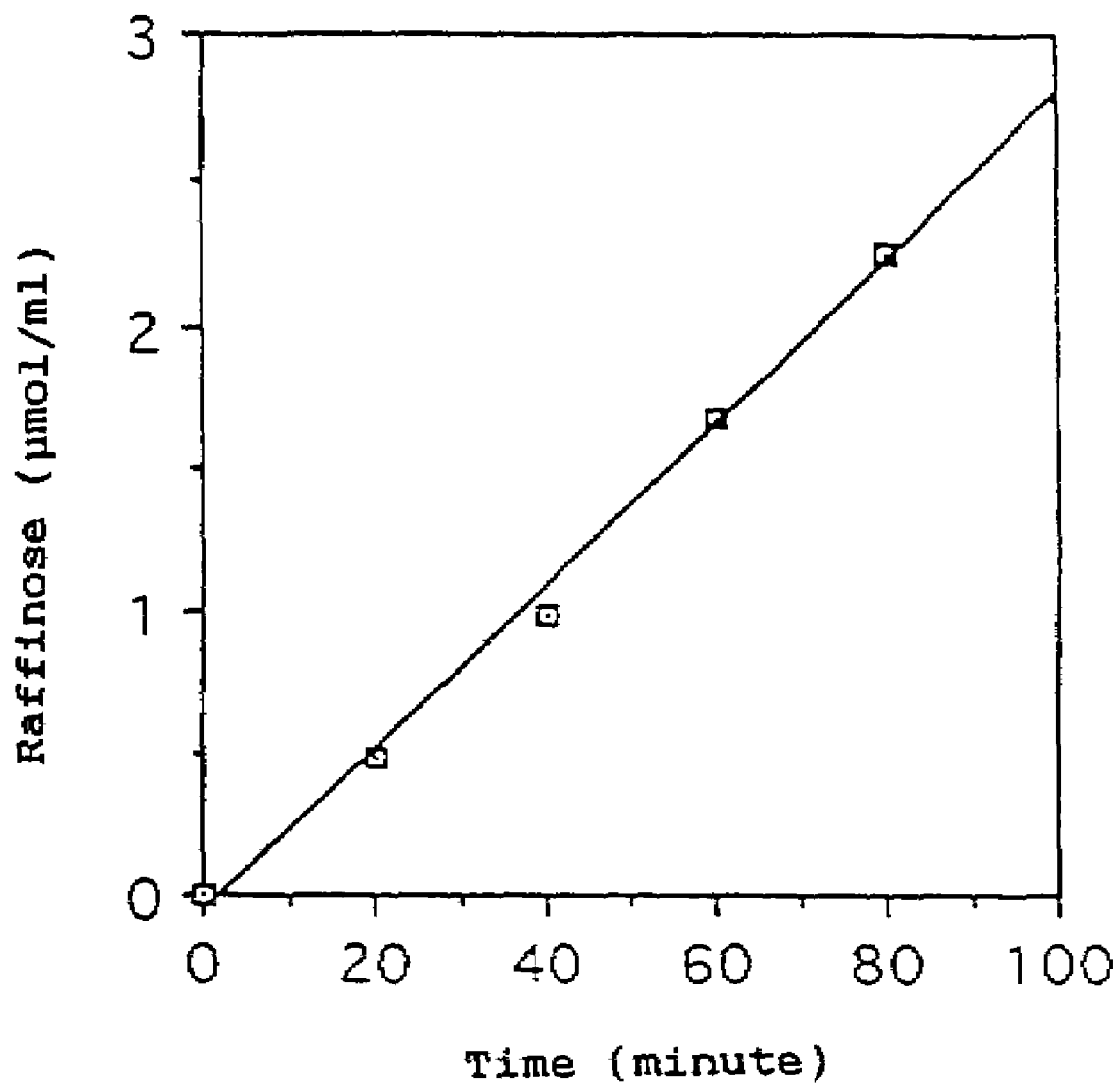
FIG. 1 shows a relationship between the reaction time and the amount of raffinose produced by the raffinose synthesis reaction.

The present invention will be more specifically explained below with reference to Examples.

At first, the method for measuring the raffinose synthase activity, used to confirm active fractions during respective purification steps and investigate characteristics of the enzyme in the following Examples, will be explained.

<Method for Measuring the Raffinose Synthase Activity>

The activity of the raffinose synthase was measured by quantitatively determining raffinose produced by the raffinose synthesis reaction by using HPLC (high-performance liquid chromatography). HPLC was performed by using Sugar Analysis System DX500 (CarboPac PA1column, pulsed amperometry detector (produced by DIONEX)).

For the raffinose synthesis reaction, to a reaction solution prepared to have a composition having the following final concentrations, 10 to 50 µl of a raffinose synthase solution was added to give a volume of 100 µl followed by performing the reaction at 32° C. for 60 minutes.

[Composition of Reaction Solution (Final Concentration)]

| | |
|---|---|
| 2.5 mM | sucrose |
| 5 mM | galactinol |
| 5 mM | DTT |
| 20 mM | Tris-HCl buffer (pH 7.0) |

After performing the reaction as described above, the reaction was stopped by adding to the reaction solution, ethanol in a volume four times the volume of the reaction solution and heating the solution at 95° C. for 30 seconds. The obtained solution was centrifuged to obtain a supernatant and the supernatant was then dried up under a reduced pressure. After that, an obtained residue was dissolved in distilled water. Raffinose in the reaction product was quantitatively determined by using the sugar analysis system to estimate the raffinose synthase activity.

EXAMPLE 1

Purification of Raffinose Synthase from Cucumber

<1> Extraction of Raffinose Synthase from Cucumber

Vein tissues were collected from true leaves of cucumber (cv.: SUYOU) obtained 6 to 10 weeks after planting. The leaf vein tissues were frozen with liquid nitrogen, and they were stored at −80° C. The frozen leaf vein tissues were ground by a mortar with liquid nitrogen, and Buffer 1 (40 mM Tris-HCl buffer (pH 7.0), 5 mM DTT, 1 mM PMSF (phenylmethanesulfonyl fluoride), 1% polyclarl AT (produced by Serva)) was added thereto to extract proteins. An obtained extract solution was filtrated with a filter such as gauze or Miracloth (produced by Calbiochem-Novobiochem). An obtained filtrate was centrifuged at 4° C. at about 30,000×g for 60 minutes. A supernatant obtained by the centrifugation was used as a crude extract solution.

<2> Anion Exchange Chromatography (1)

The crude extract solution (about 560 ml) obtained as described above was applied to a column system comprising five connected columns for strongly basic anion exchange chromatography (HiTrap Q, produced by Pharmacia, 1.6 cm×2.5 cm) equilibrated with Buffer 2 (20 mM Tris-HCl buffer (pH 7.0), 5 mM DTT) to adsorb the raffinose synthase activity to the columns. Subsequently, the columns were washed with Buffer 3 (20 mM Tris-HCl buffer (pH 7.0), 0.2 M NaCl, 5 mM DTT) in a volume five times of the columns so that non-adsorbed proteins were washed out. After that, the raffinose synthase activity was eluted from the columns with 50 ml of Buffer 4 (20 mM Tris-HCl buffer (pH 7.0), 0.3 M NaCl, 5 mM DTT).

<3> Anion Exchange Chromatography (2)

The eluted solution (about 75 ml) was placed in a dialysis tube (Pormembranes MWC O: 10,000, produced by Spectra), and it was dialyzed against 10 L of Buffer 5 (20 mM Tris-HCl buffer (pH 7.0), 0.05 M NaCl, 5 mM DTT) at 4° C. overnight. The dialyzed sample was applied to a column for weakly basic anion exchange chromatography (DEAE-TOYOPE-ARL, produced by Tosoh Corp., 2.2×20 cm) equilibrated with Buffer 5 to adsorb the raffinose synthase activity to the column. Subsequently, the column was washed with Buffer 5 in a volume five times the volume of the column to wash out non-adsorbed proteins. After that, a linear concentration gradient of 0.05 M to 0.35 M NaCl in a volume twenty times the volume of the column was applied to elute the enzyme activity so that fractionation was performed.

<4> Gel Filtration Chromatography

The eluted solution obtained as described above (about 160 ml) was concentrated into 6.5 ml by using a concentrator (Centriprep 10, produced by Amicon). Aliquots (each 3 ml) of the concentrated solution were applied to a column for gel filtration chromatography (Superdex 200 pg, produced by Pharmacia, 2.6 cm×60 cm). Equilibration for the column and elution from the column were performed by using Buffer 6 (20 mM Tris-HCl buffer (pH 7.0), 0.1 M NaCl, 5 mM DTT, 0.02% Tween 20). Fractions having the raffinose synthase activity were collected from fractionated fractions.

<5> Hydroxyapatite Chromatography

A collected fraction (about 25 ml) having the raffinose synthase activity fractionated by the gel filtration was concentrated by using Centriprep 10, and the buffer was exchanged with Buffer 7 (0.01 M sodium phosphate buffer (pH 7.0), 5 mM DTT, 0.02% Tween 20). An obtained concentrate solution (about 1.2 ml) was applied to a hydroxyapatite column (Bio-Scale CHT-1, produced by Bio Rad, 0.7× 5.2) previously equilibrated with the same buffer to adsorb the raffinose synthase activity. The column was washed with the same buffer in a volume (10 ml) five times the volume of the column. After that, a linear concentration gradient of 0.01 M to 0.3 M phosphate in a volume twenty times the volume of the column was applied to elute the enzyme activity so that fractionation was performed.

<6> Hydroxyapatite Rechromatography

An active fraction obtained in accordance with the hydroxyapatite chromatography as described above was subjected to rechromatography in the same manner as described above to obtain a purified raffinose synthase fraction (about 2 ml).

The amount of protein contained in the active fraction was about 200 µg. The total activity was 5700 nmol/hour, and the specific activity per protein was about 28 µmol/hour/mg. The active fraction contained only a protein which exhibited a single band corresponding to a molecular weight of 90 kDa to 100 kDa on electrophoresis as described later. The specific activity of the obtained purified enzyme sample was about 2000 times that of the crude extract solution. The recovery was 12% with respect to the amount of the enzyme obtained after the strongly basic anion exchange chromatography using HiTrap Q. Results of the purification are summarized in Table 1.

TABLE 1

|  | Total protein mg | Total activity nmol/h | Specific activity nmol/h/mg | Yield % |
|---|---|---|---|---|
| Crude extract | 1915 | 20700 | 11 | — |
| HiTrap Q | 1092 | 48800 | 45 | 100 |
| DEAE-TOYOPEARL | 540 | 33000 | 61 | 68 |
| Superdex 200 pg | 1.79 | 26500 | 14800 | 54 |
| Apatite (1)* | 0.51 | 12600 | 24700 | 26 |
| Apatite (2)* | 0.20 | 5700 | 28500 | 12 |

Apatite (1)*: Hydroxyapatite chromatography (1)
Apatite (2)*: Hydroxyapatite chromatography (2)

EXAMPLE 2

Investigation on Characteristics of Raffinose Synthase

Characteristics of the purified raffinose synthase obtained in Example 1 were investigated.

<1> Molecular Weight Measurement (1) Gel Filtration Chromatography

An aliquot (10 µl) of the purified raffinose synthase was dispensed. This sample and a molecular weight marker (Molecular Weight Marker Kit for Gel Filtration, produced by Pharmacia) were applied to a gel filtration chromatography column (Superdex 200 pg, produced by Pharmacia). Equilibration of the column and elution from the column were performed by using Buffer 6 (20 mM Tris-HCl buffer (pH 7.0), 0.1 M NaCl, 5 mM DTT, 0.02% Tween 20). As a result, the molecular weight of the raffinose synthase was estimated to be about 75 kDa to 95 kDa.

(2) Polyacrylamide Gel Electrophoresis (Native PAGE)

An aliquot (10 µl) of the purified raffinose synthase was dispensed, and the same volume of a sample buffer (0.0625 M Tris-HCl (pH 6.8), 15% glycerol, 0.001% BPB) was added thereto to prepare an electrophoresis sample. The sample (10 µl) was applied to 10% polyacrylamide gel (produced by Daiichi Chemical, Multigel 10), and electrophoresed at 40 mA for about 60 minutes with 0.025 M Tris—0.192 M glycine buffer (pH 8.4). After the electrophoresis, the gel was stained with Silver Stain Kit (produced by nacalai tesque). As a result, the molecular weight was estimated to be about 90 kDa to 100 kDa.

(3) SDS-polyacrylamide Gel Electrophoresis (SDS-PAGE)

Figure 2:
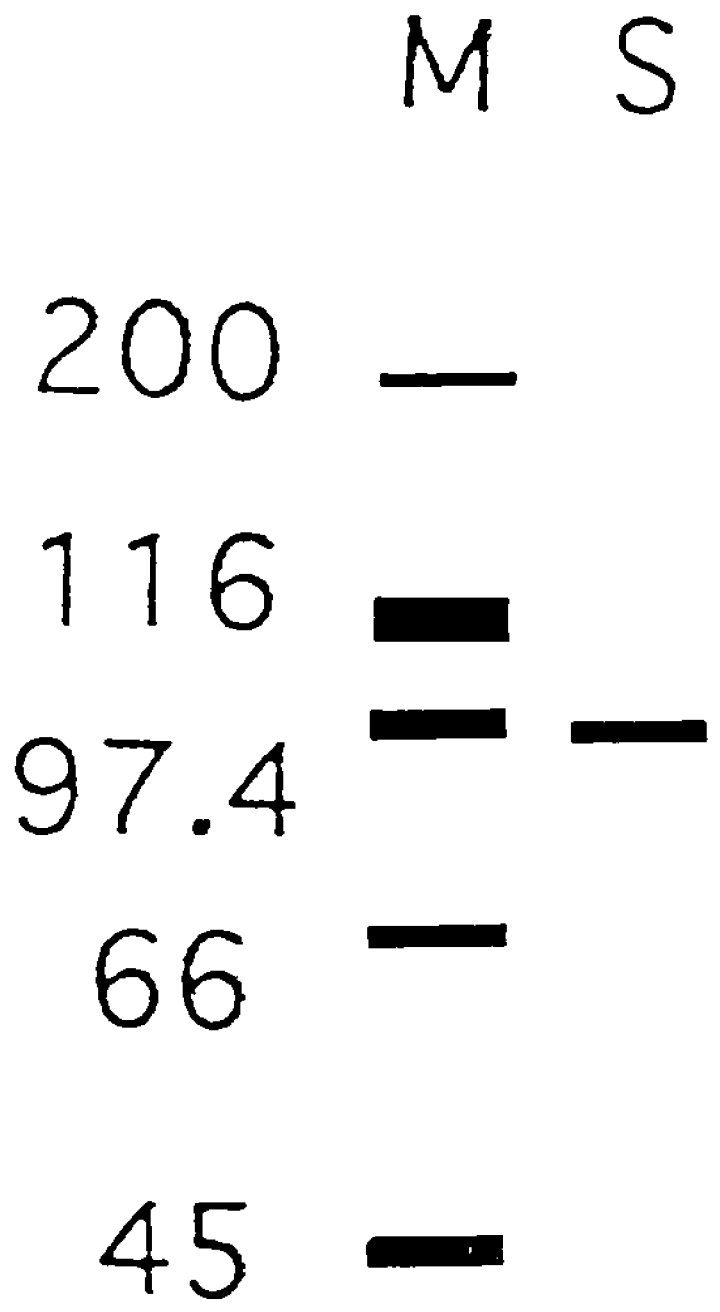

An aliquot (10 µl) of the purified raffinose synthase was dispensed, and the same volume of a sample buffer (0.0625 M Tris-HCl (pH 6.8), 2% SDS, 10% glycerol, 5% mercaptoethanol, 0.001% BPB) was added thereto, followed by heating in a boiling water bath for 1 minute to prepare an electrophoresis sample. The sample (10 µl) was applied to 10 to 20% gradient polyacrylamide gel (produced by Daiichi Chemical), and electrophoresed at 40 mA for about 70 minutes with 0.025 M Tris—0.192 M glycine buffer (pH 8.4) containing 0.1% SDS. After the electrophoresis, the gel was stained with Silver Stain Kit (produced by nacalai tesque). A result is shown in FIG. 2. As a result, the molecular weight was estimated to be about 90 kDa to 100 kDa.

<2> Optimum Reaction Temperature

Figure 3:
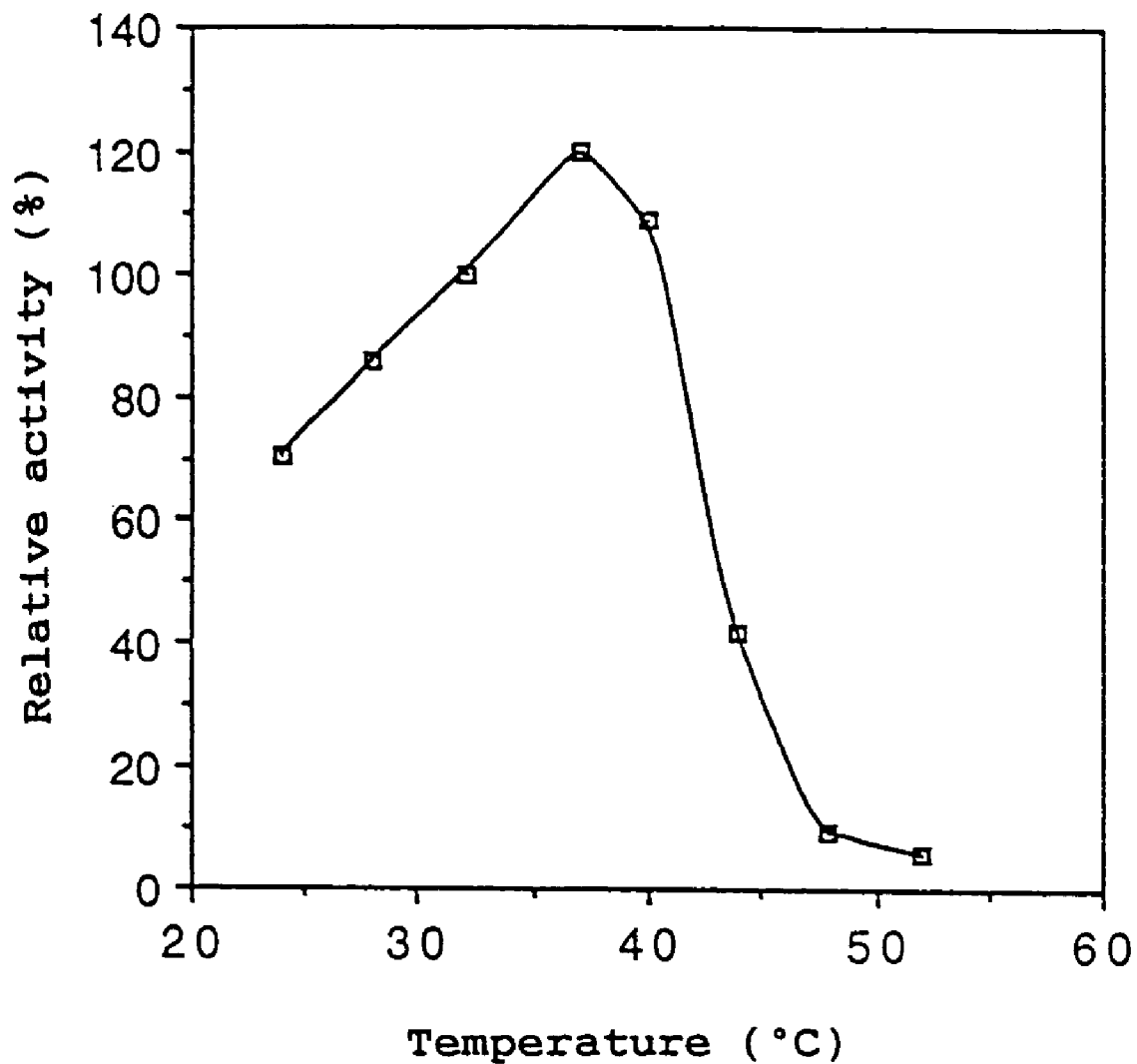
FIG. 3 shows an influence of the reaction temperature on the raffinose synthase activity.

The raffinose synthase activity was measured under various temperature conditions (28° C., 32° C., 36° C., 40° C., 44° C., 48° C., and 52° C.) in accordance with the method for measuring the raffinose synthase activity described above. The enzyme solution was added to each of the reaction solutions in an amount of 2 μl. FIG. 3 shows relative activities at the respective temperatures assuming that the enzyme activity at 32° C. was 100. As a result, the raffinose synthase exhibited the activity in a range of about 25 to 42° C., and the optimum reaction temperature was about 35 to 40° C.

<3> Optimum Reaction pH

Figure 4:
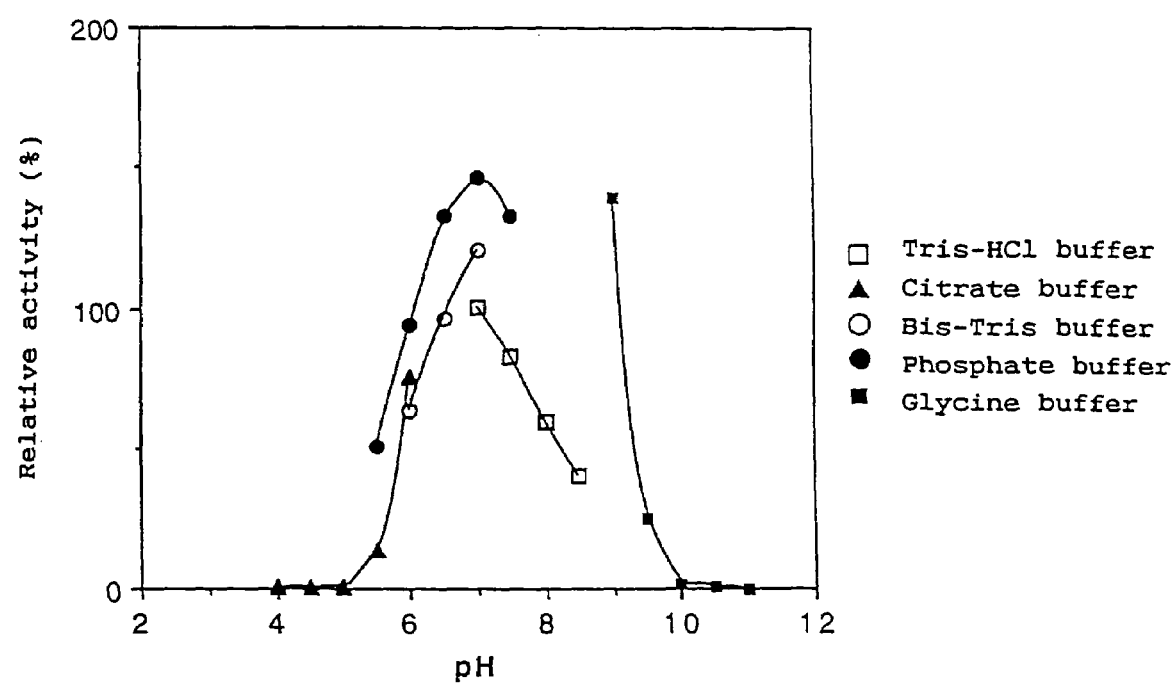
FIG. 4 shows an influence of the reaction pH on the raffinose synthase activity.

The raffinose synthase activity was measured under various pH conditions (pH 4 to 11) in accordance with the method for measuring the raffinose synthase activity described above. The reactions were performed by using 50 mM citrate buffer (pH 4 to 6), 50 mM potassium phosphate buffer (pH 5.5 to 7.5), 50 mM Bis-Tris buffer (pH 6 to 7), 20 mM Tris-HCl buffer (pH 7 to 8.5), and 50 mM glycine-NaOH buffer (pH 9 to 11). The enzyme solution was added to the respective reaction solutions in an amount of 2 μl. A result is shown in FIG. 4.

As a result, the raffinose synthase exhibited the activity in a range of pH 5 to 10, and the optimum reaction pH was about 6 to 8, provided that the activity varied depending on the type of the buffer used for the measurement.

<4> Investigation on Inhibitors and Metal Ions

Various enzyme inhibitors or metal ions were added to the reaction solution of the purified raffinose synthase to give a final concentration of 1 mM respectively, and the raffinose synthase activity was measured in the same manner as described above. Table 2 shows remaining activities with respect to the enzyme activity obtained when neither inhibitor nor metal ion was added. Iodoacetamide and N-ethylmaleimide remarkably inhibited the enzyme activity. The inhibiting effect was scarcely observed for $CaCl_2$, $CuCl_2$, and $MgCl_2$. However, $MnCl_2$, $ZnCl_2$, and $NiCl_2$ exhibited the inhibiting effect.

TABLE 2

| Inhibitor or metal ion | Remaining activity (%) |
|---|---|
| No addition | 100 |
| Iodoacetoamide | 0 |
| N-ethylmaleimide | 40 |
| $CaCl_2$ | 115 |
| $CuCl_2$ | 101 |
| $MgCl_2$ | 96 |
| $MnCl_2$ | 32 |
| $ZnCl_2$ | 42 |
| $NiCl_2$ | 68 |

<5> Inhibition by Myo-inositol

Figure 5:
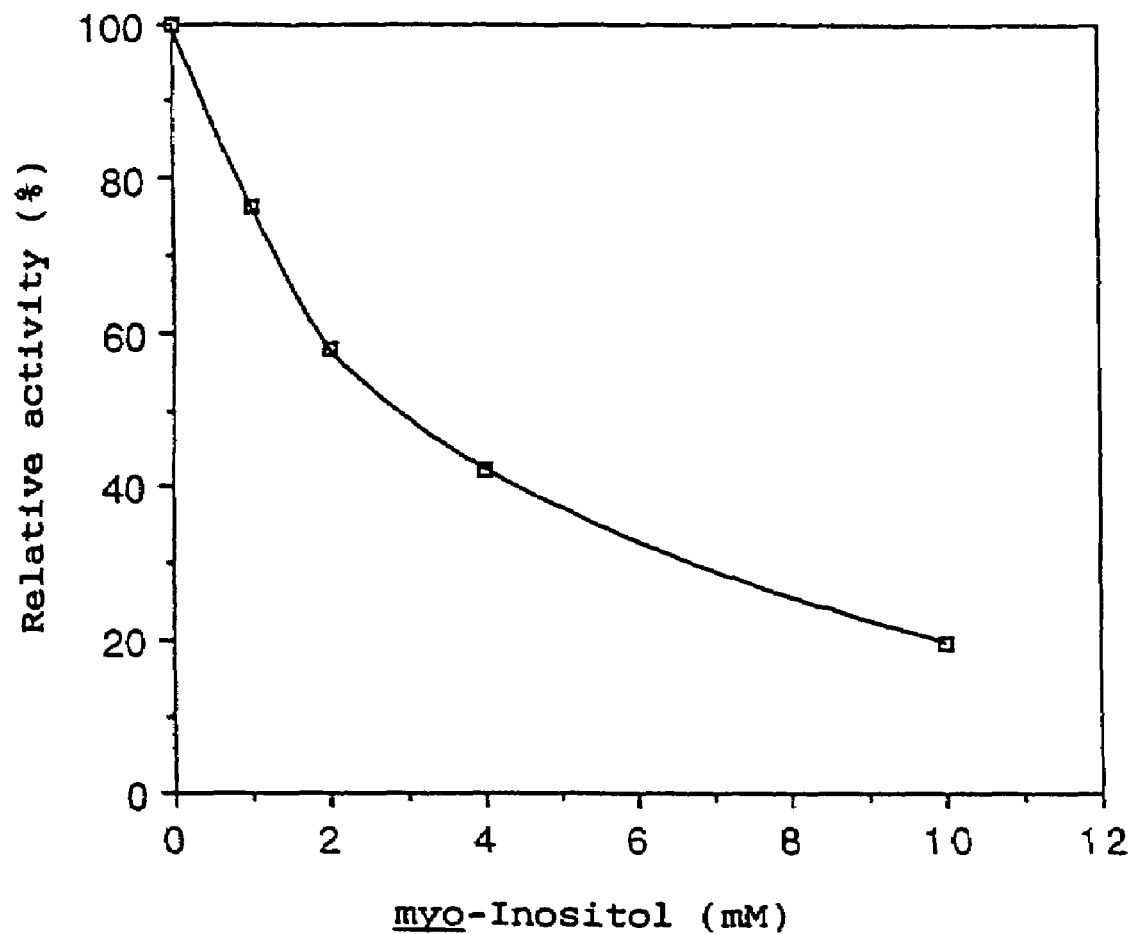
FIG. 5 shows an influence of myo-inositol on the raffinose synthase activity.

Investigation was made for inhibition by myo-inositol as the reaction product of the raffinose synthesis reaction. To the reaction solution, myo-inositol was added at various concentrations, and the raffinose synthase activity was measured. A result is shown in FIG. 5. The enzyme activity was inhibited as the concentration of added myo-inositol was increased.

<6> Stable pH

Figure 6:
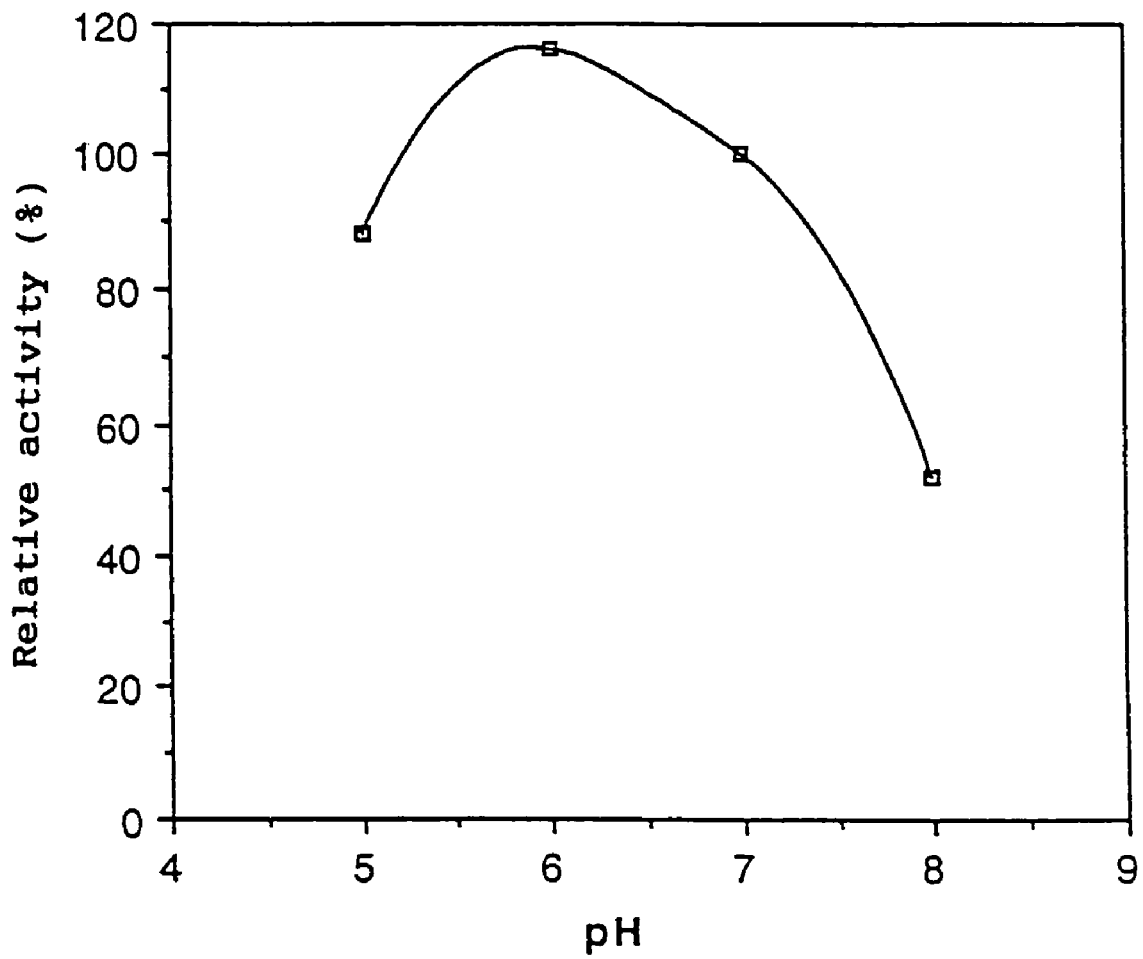
FIG. 6 shows a stable pH range of the raffinose synthase.

The raffinose synthase fraction obtained by the anion exchange chromatography (2) described above was incubated for 4 hours at 4° C. in 50 mM Bis-Tris-HCl buffer (pH 5 to 8.0, containing 0.5 mM DTT) or 20 mM Tris-HCl buffer (pH 7 to 8.0, containing 0.5 mM DTT), and then the raffinose synthase activity was measured. FIG. 6 shows the enzyme activity versus pH of the buffer used for the incubation. The raffinose synthase activity was confirmed after the incubation under any of the incubation conditions. Especially, the enzyme was stable in a range of pH 5 to 7.5.

<7> Stable Temperature

The raffinose synthase fraction obtained by the anion exchange chromatography (2) described above was incubated in 20 mM Tris-HCl buffer (pH 7, containing 0.5 mM DTT) for 60 minutes at 28° C., 32° C., 37° C., or 40° C., and then the raffinose synthase activity was measured. As a result, the enzyme of the present invention exhibited, in the range of 28° C. to 40° C., activities of 80% to 100% of that obtained by a control for which the incubation treatment was not performed for comparison, and therefore was stable in the range.

<8> Analysis of Amino Acid Sequence

The cysteine residue of the purified raffinose synthase was subjected to reducing pyridylethylation, and the reaction mixture was desalted. An obtained sample was digested at 37° C. for 12 hours with lysylendopeptidase (Achromobacter protease 1, produced by Wako Pure Chemical Industries) to form peptide fragments. An obtained peptide mixture was applied to reverse phase HPLC (column: Waters μBondasphere (φ2.1×150 mm, $C_{18}$, 300 Å, produced by Waters (Millipore))) to separate and obtain the respective peptide fragments. 0.1% TFA (trifluoroacetic acid) was used as a solvent, and elution was performed with a concentration gradient of acetonitrile. Amino acid sequences of three fragments selected from the obtained peptide fragments were determined by using a protein sequencer. The determined amino acid sequences of the respective peptides are shown in SEQ ID NOs: 1 to 3 in Sequence Listing. These peptides will be thereafter referred to as Peptides 1, 2, and 3 respectively in this order.

EXAMPLE 3

Preparation of DNA Coding for Raffinose Synthase Originating from Cucumber

<1> Isolation of Partial Fragment of cDNA of Raffinose Synthase by Means of PCR Method Major veins (22 g) of cucumber were ground by a mortar with liquid nitrogen. The ground material was added to a mixture of an extraction buffer (100 mM lithium chloride, 100 mM Tris-HCl (pH 8.0), 10 mM EDTA, and 1% SDS) and an equal amount of phenol previously heated to 80° C., followed by agitation. After that, a mixture of phenol and an equal amount of chloroform:isoamyl alcohol (24:1) was added thereto, followed by agitation again. An obtained mixture solution was centrifuged at 4° C. at 9250×g for 15 minutes to collect a supernatant. The supernatant was repeatedly subjected to the treatment with phenol and the treatment with chloroform:isoamyl alcohol to obtain a supernatant after centrifugation. To the supernatant, an equal amount of 4 M lithium chloride was added, followed by being stationarily left to stand at −70° C. for 1 hour.

After thawing at room temperature, the sample was centrifuged at 4° C. at 9250×g for 30 minutes to obtain a precipitate. The precipitate was washed with 2 M lithium chloride once and with 80% ethanol once. After drying, the precipitate was dissolved in 2 ml of a diethylpyrocarbonate-treated solution to give a sample of purified total RNA. The obtained total RNA was 2.38 mg.

The all amount of the total RNA was applied to poly(A)$^+$ RNA purification kit (produced by STRATAGENE CLONING SYSTEMS) using an oligo(dT) cellulose column, so that poly(A)$^+$RNA molecules were purified to obtain 42.5 μg of poly(A)$^+$RNA.

Single strand cDNAs were synthesized from poly(A)$^+$ RNA obtained as described above, by using reverse transcriptase Super Script II (produced by GIBCO BRL). In order to isolate raffinose synthase cDNA from an obtained cDNA mixture, amplification was performed in accordance with the PCR method. As primers in PCR, single strand oligonucleotides (SEQ ID NOs: 6 to 22) shown in FIG. 7 were synthesized on the basis of the amino acid sequences of the peptide fragments of the raffinose synthase originating from cucumber, determined in Example 2. In the sequences of the respective primers, R represents A or G, Y represents C or T, M represents A or C, K represents G or T, D represents G, A, or T, H represents A, T, or C, B represents G, T, or C, N represents G, A, T, or C, and I represents inosine (base: hypoxanthine) respectively.

A DNA fragment of about 540 base pairs was amplified when the primers were combined such that the 5'-side primer was A (A1 (SEQ ID NO: 6), A2 (SEQ ID NO: 7), A3 (SEQ ID NO: 8), A4 (SEQ ID NO: 9)) and the 3'-side primer was D' (D'1 (SEQ ID NO: 21), D'2 (SEQ ID NO: 22)), or the 5'-side primer was C2 (SEQ ID NO: 14) and the 3'-side primer was B'1 (SEQ ID NO: 18) or B'2 (SEQ ID NO: 19). The fragment was cloned into a plasmid pCRII by using TA cloning kit (produced by INVITROGEN BV) to analyze its nucleotide sequence. As a result, a nucleotide sequence coding for the amino acid sequences of Peptides 1, 2 was found inwardly between the primer sequences at both terminals. Accordingly, it was found that the amplified fragment is a DNA fragment originating from the raffinose synthase gene.

In order to specify the position of the cloned PCR-amplified DNA fragment on the raffinose synthase gene, 3'-RACE was performed by using RACE kit (3' Ampifinder RACE Kit, produced by CLONTACH).

PCR was performed by using the cDNA mixture as a template, C (C1 (SEQ ID NO: 13), C2 (SEQ ID NO: 14)) as a 5'-side primer, and a primer having oligo(dT) and an anchor sequence as a 3'-side primer. Further, PCR was performed by using an amplified fragment thus obtained as a template, D (D1 (SEQ ID NO: 15), D2 (SEQ ID NO: 16)) located inwardly from C as a 5'-side primer, and an oligo(dT)-anchor primer as a 3'-side primer. As a result, a DNA fragment of about 2400 base pairs was amplified only when PCR was performed by using, as the template, DNA amplified with C1 (SEQ ID NO: 13) or C2 (SEQ ID NO: 14) and the oligo(dT)-anchor primer, and using D2 (SEQ ID NO: 16) and the oligo (dT)-anchor primer. Further, PCR was performed by using C (C1 (SEQ ID NO: 13), C2 (SEQ ID NO: 14)) as the 5'-side primer and the oligo(dT)-anchor primer as the 3'-side primer, and then PCR was performed by using the amplified fragment thus obtained as a template, E (SEQ ID NO: 17) as a 5'-side primer, and the oligo(dT)-anchor primer as a 3'-side primer. As a result, a DNA fragment of about 300 base pairs was amplified in any case.

Similarly, PCR was performed by using A (A1 (SEQ ID NO: 6), A2 (SEQ ID NO: 7), A3 (SEQ ID NO: 8), or A4 (SEQ ID NO: 9)) as a 5'-side primer, and the primer having oligo (dT) and the anchor sequence as a 3'-side primer. Further, PCR was performed by using an amplified fragment thus obtained as a template, and using B (B1 (SEQ ID NO: 10), B2 (SEQ ID NO: 11), or B3 (SEQ ID NO: 12)) located inwardly from A as a 5'-side primer, and the same oligo(dT)-anchor primer as a 3'-side primer. As a result, a DNA fragment of about 2000 base pairs was obtained when the B2 primer was used even in the case that any of the A primers was used. Thus the DNA fragment amplified by using the A2 and B2 primers was cloned. As a result of nucleotide sequence analysis, the DNA fragment included, on the 5'-side, the nucleotide sequence coding for the amino acid sequence of Peptide fragment 1 used to prepare the primer. The DNA fragment also included, on the 3'-side, the poly(A) sequence and the nucleotide sequence corresponding to Peptide fragment 3 at a position located upstream therefrom.

In view of the result of PCR described above, it was found that Peptide fragments of the raffinose synthase are arranged from the N-terminal side in an order of 2, 1, 3, and the DNA fragment of about 540 base pairs previously obtained by PCR was a portion located near to the 5'-terminal on the raffinose synthase gene. In order to screen a cDNA clone containing the entire length of the raffinose synthase gene, it is desirable that DNA to be used as a probe can detect a portion near to the 5'-terminal side. Accordingly, the obtained DNA fragment was used as a probe to perform screening for a cDNA library.

<2> Cloning of Entire Length of Coding Region of Raffinose Synthase cDNA

At first, a cDNA library was prepared as follows. Double strand cDNAs were synthesized from poly(A)$^+$RNA (3.8 µg) obtained in the foregoing item <1> by using Time Saver cDNA synthesis kit (produced by Pharmacia Biotech). Obtained cDNAs were incorporated into EcoRI restriction enzyme cleavage site of λ phage vector, λMOSSlox (produced by Amersham) respectively, and then incorporated into the phage protein by using GigapackII Gold packaging kit (produced by STRATAGENE CLONING SYSTEMS). Thus the cucumber cDNA library was prepared. This library had a titer of $1.46 \times 10^7$ pfu/µg vector.

Host cells of *Escherichia coli* ER1647 were infected with the phages contained in the cucumber cDNA library in an amount corresponding to $1.4 \times 10^5$ pfu, and then the cells were spread over 14 agar plates each having a diameter of 90 mm to give $1.0 \times 10^4$ pfu per plate. The cells were cultivated at 37° C. for about 6.5 hours. After that, phage plaques formed on the plates were transferred to nylon membranes (Hybond-N+, produced by Amersham).

Next, the nylon membranes were treated with alkali to denature transferred DNA, followed by neutralization and washing. After that, the nylon membranes were treated at 80° C. for 2 hours to fix DNA on the membranes.

Positive clones were screened on the obtained nylon membrane by using the DNA fragment of about 540 base pairs obtained in the foregoing item <1> as a probe. The DNA fragment of about 540 base pairs was digested with restriction enzyme EcoRI, followed by electrophoresis to excise and purify only the insert of about 540 base pairs. The insert was labeled with fluorescein by using DNA labeling and detection system (Gene Images labeling and detection system, produced by Amersham) to be used as the probe. The nylon membranes were subjected to prehybridization at 60° C. for 30 minutes, and then the labeled probe was added to perform hybridization at 60° C. for 16 hours. An antibody (alkaline phosphatase-labeled anti-fluorescein antibody) for detecting the labeled DNA was used after being diluted 50000 times. In this screening process, candidate strains for positive clones were obtained. The obtained candidate strains were further subjected to repeated screening twice in the same manner as described above to obtain a purified positive clone.

*Escherichia coli* BM25.8 was infected with the positive clone, and it was cultivated on a selection medium containing carbenicillin. A plasmid vector λMOSSlox-CRS containing cDNA was excised therefrom. The inserted cDNA of the plasmid had a length of about 2.5 kb. *Escherichia coli* JM109 was transformed with the plasmid. Plasmid DNA was prepared from a transformant, and was used as a sample for analyzing the nucleotide sequence.

The nucleotide sequence of the inserted cDNA was analyzed by using Taq DyeDeoxy Terminator Cycle Sequencing Kit (produced by Perkin-Elmer) in accordance with the conventionally known method.

As a result, a nucleotide sequence comprising 2352 base pairs as shown in SEQ ID NO: 4 in Sequence Listing was revealed. The sequence included a portion coincident with the nucleotide sequence of the DNA probe used by the present inventors. An amino acid sequence translated from the nucleotide sequence is shown in SEQ ID NOs: 4 and 5. The amino acid sequence included portions coincident with Peptide 1 (amino acid numbers of 215 to 244 in SEQ ID NO: 5), Peptide 2 (amino acid numbers of 61 to 79 in SEQ ID NO: 5), and Peptide 3 (amino acid numbers of 756 to 769 in SEQ ID NO: 5) of the raffinose synthase originating from cucumber obtained by the present inventors. Thus it was confirmed that the amino acid sequence codes for the raffinose synthase.

The transformant, designated as AJ13263, of *Escherichia coli* JM109, which harbors the plasmid pMossloxCRS containing DNA coding for the raffinose synthase obtained as described above, has been internationally deposited on the basis of the Budapest Treaty since November 19, 1996 in National Institute of Bioscience and Human Technology of Agency of Industrial Science and Technology of Ministry of International Trade and Industry (postal code: 305, 1-3 Higashi 1-chome, Tsukuba-shi, Ibaraki-ken, Japan), and awarded an accession number of FERM BP-5748.

EXAMPLE 4

Preparation of DNA Coding for Raffinose Synthase Originating from Soybean

<1> Screening of Probe for Cloning Raffinose Synthase Gene Originating from Soybean Northern hybridization to soybean total RNA was carried out by using the entire length of the raffinose synthase gene originating from cucumber as probe. The probe was prepared by digesting the plasmid pMossloxCRS obtained in Example 3 with a restriction enzyme NotI, subjecting the digest to agarose gel electrophoresis to isolate an inserted fragment and labeling the isolated DNA fragment with α-$P^{32}$ dCTP. As the total RNA, 30 μg of total RNA prepared from immature seeds (5 to 6 weeks after bloom) of soybean by the SDS-phenol method. After prehybridization for 30 minutes, the probe was added to carry out hybridization at 42° C. overnight. Washing was carried out under a condition of 1×SSC, 0.1% SDS, and 60° C. The signal of the raffinose synthase originating from cucumber as a control was observed, but no distinct signal was observed with respect to the RNA originating from soybean. It was considered that it was desirable to use a more conserved region rather than the entire length of the cucumber gene.

<2> Isolation of Partial Fragment of Raffinose Synthase Gene of *Arabidopsis thaliana*

Pods 17 to 20 days after bloom (125 mg) of *Arabidopsis thaliana* were ground by a mortar with liquid nitrogen. To the ground material, 3 ml of 2×CTAB (2% cetyltrimethylammonium bromide, 0.1 M Tris-HCl (pH 9.5), 1.4 M NaCl, and 0.5% mercaptoethanol) was added, and allowed to diffuse therein, followed by agitation at 65° C. for 10 minutes. After the mixture was transferred to Bluemax (50 ml; Falcon Tube), 3 ml of chloroform:isoamyl alcohol (24:1(v:v)) was added thereto, followed by gentle agitation. An obtained mixture solution was centrifuged at 12000 rpm for 10 minutes to collect a supernatant. The supernatant was again extracted with chloroform:isoamyl alcohol (24:1(v:v)) to obtain a supernatant after centrifugation at 10000 rpm for 25 minutes. To 1.8 ml of the supernatant, 1.5 ml of isoamyl alcohol was added and mixed to obtain a precipitate after centrifugation at 12000 rpm for 15 minutes at 4° C. The precipitate was washed with 70% ethanol and dried, and then dissolved in 1 ml of TE buffer. To the solution, a quarter amount of 10 M lithium chloride was added and mixed, and allowed to stand on ice for 4 hours. After centrifugation at 12000 rpm for 15 minutes at 4° C., a precipitate was washed with 2 M lithium chloride, and with 70% ethanol, dried and then dissolved in 100 μl of TE buffer. To the solution, phenol:chloroform (1:1(v/v)) was added and agitated to an aqueous layer after centrifugation at 12000 rpm for 15 minutes at 4° C. The aqueous layer was subjected to ethanol precipitation, and an obtained precipitate was washed with 70% ethanol and dried, and then dissolved in 10 μl of a diethylpyrocarbonate-treated solution to give a sample of purified total RNA. The obtained total RNA was 18.7 μg. Single strand cDNAs were synthesized from the total RNA by using reverse transcriptase Super Script II (produced by GIBCO BRL).

In order to amplify a partial fragment of the raffinose synthase gene from an obtained cDNA mixture in accordance with the PCR method, primers were synthesized. DNAs having homology with the raffinose synthase gene originating from cucumber were searched on GenBank, and primers were synthesized as single strand oligonucleotides (SEQ ID NOs: 25 and 26) on the basis of the conserved region. A DNA fragment of about 250 base pairs was amplified when PCR was carried out by using the primers and the single strand cDNA as a template. The fragment was cloned into a plasmid pCRII by using TA cloning kit (produced by INVITROGEN BV) to analyze its nucleotide sequence. As a result, a nucleotide sequence shown in SEQ ID NO: 27 was obtained. It was considered that the partial cDNA fragment of the raffinose synthase originating from *Arabidopsis thaliana*, which had homology with the raffinose synthase originating from cucumber, was obtained.

<3> Cloning of cDNA of Raffinose Synthase Originating from Soybean

Seeds 5 to 6 weeks after bloom (4.5 g) of soybean were ground by a mortar with liquid nitrogen. From the ground material, 1.3 mg of total RNA was prepared by SDS-phenol method. The total RNA was applied to an oligo(dT) cellulose column (poly(A)$^+$RNA purification kit; produced by STRATAGENE CLONING SYSTEMS) to isolate about 6 μg of poly(A)$^+$RNA. From about 2 μg of poly(A)$^+$RNA obtained, double strand cDNAs were synthesized using Time Saver cDNA synthesis kit (produced by Pharmacia Biotech) with oligo dT primers. Obtained cDNAs were incorporated into EcoRI restriction enzyme cleavage site of λ phage vector, λMOSSlox (produced by Amersham) respectively, and then incorporated into the phage particles by using GigapackII Gold packaging kit (produced by STRATAGENE CLONING SYSTEMS). Thus the soybean cDNA library was prepared. This library had a titer of 1.42×10$^7$ pfu/pg vector.

Phages contained in the soybean cDNA library in an amount corresponding to 1.4×10$^5$ pfu were transferred and fixed to nylon membrans (Hybond-N+, produced by Amersham) as in the cucumber cDNA library. With respect to each plate, transfer to two membranes was carried out to prepare two sets. The obtained membranes were screened by using the partial cDNA fragment of the raffinose synthase originating from *Arabidopsis thaliana*. This DNA fragment was used as a probe by labelling with fluorescein by Gene Image labelling detect system (produced by Amersham). Hybridization and detection were carried out as in the cucumber cDNA library screening, except that washing of the membrane was carried out at 1×SSC and 0.1% SDS for one on the sets and at 0.1×SSC and 0.1% SDS for another. 15 of positive clone candidates were obtained under both conditions. As to the candidates, screening as described above was once repeated to obtain 5 purified clones.

Escherichia coli BM25.8 was infected with each of the positive clones, and a plasmid containing the cDNA was excised therefrom. Also, Escherichia coli JM109 was transformed with the plasmid, and plasmid DNA was prepared from the transformant and used as a sample for sequence analysis. Sequence analysis was carried out in the same manner as in the case of the raffinose synthase gene originating from cucumber. Based on the sequence analysis, it was confirmed that one of 5 clones, pMOSSloxSRS contained the entire length of the raffinose synthase gene originating from soybean.

The insert fragment of pMOSSloxSRS had a nucleotide sequence comprising 2780 base pairs as shown in SEQ ID NO: 23 in Sequence Listing, and encoded the raffinose synthase composed of 750 amino acids. The insert fragments of other clones were shorter than that of pMOSSloxSRS and lacked 5' side of the raffinose synthase.

The transformant, designated as AJ13379, of Escherichia coli JM109, which harbors the plasmid pMOSSloxSRS containing a DNA fragment containing DNA coding for the raffinose synthase obtained as described above, has been internationally deposited on the basis of the Budapest Treaty since Oct. 20, 1997 in National Institute of Bioscience and Human Technology of Agency of Industrial Science and Technology of Ministry of International Trade and Industry (postal code: 305, 1-3 Higashi 1-chome, Tsukuba-shi, Ibaraki-ken, Japan), and awarded an accession number of FERM BP-6149.

EXAMPLE 5

Chimeric Gene and Transformed Plant Containing DNA Coding for Raffinose Synthase <1> Construction of Plasmid Containing Chimeric Gene The DNA fragment coding for the raffinose synthase was introduced into *Arabidopsis thaliana* by using LBA4404 as *Agrobacterium* and pBI121 (produced by CLONTECH) as a binary vector. pBI121 is a plasmid originating from pBIN19, which comprises nopaline synthase gene promoter connected to neomycin phosphotransferase structural gene (NPTII), nopaline synthase gene terminator (Nos-ter), CaMV 35S promoter, GUS (β-glucuronidase) gene, and Nos-ter, and which has sequences for enabling transposition to plant, on both sides thereof. A SmaI site is located downstream from CaMV 35S promoter. An insert inserted into this site is expressed under the regulation of the promoter.

A fragment of the raffinose synthase gene originating from cucumber obtained in Example 3 was inserted into the binary vector pBI121. The raffinose synthase gene was digested with DraI to prepare, by means of agarose gel electrophoresis, a DNA fragment containing 1382nd to 2529th nucleotides in SEQ ID NO: 4 in Sequence Listing. This fragment was ligated into the SmaI site of pBI121. *Escherichia coli* HB101 was transformed with the ligation reaction solution to obtain transformant strains, and recombinant plasmids were prepared therefrom. Two recombinant plasmids, in which the raffinose synthase DNA fragment was reversely connected to CaMV 35S promoter (antisense), and the raffinose synthase DNA fragment was connected to CaMV 35S promoter in the ordinary direction (sense), were selected from the obtained recombinant plasmids. The two recombinant plasmids were designated as pBIcRS1 and pBIcRS9 respectively.

Also, a plasmid containing a chimeric gene expressing the raffinose synthase was constructed. pMOSSloxSRS containing the raffinose synthase gene was digested with NotI and a raffinose synthase gene fragment was prepared by means of agarose gel electrophoresis. The NotI cleavage sites of the DNA fragment were filled in by the Taq polymerase reaction using dNTP to obtain a SRS fragment having A bases protruded at 3' side. On the other hand, pBI121 was digested with SmaI, a linear DNA was purified by means of agarose gel electrophoresis, and pBI121/SmaI having T bases added at 3' side was obtained by the Taq polymerase reaction using dTTP. After purification, the SRS fragment was ligated to pBI121/SmaI. *Escherichia coli* HB101 was transformed with the ligation reaction solution. Plasmid DNAs were prepared from the obtained transformants and digested with each of restriction enzymes EcoRI, BamHI, XhoI or a combination thereof. Molecular weights of the obtained fragments were determined by agarose gel electrophoresis to prepare a physical map. Based on the prepared physical map, one in which the raffinose synthase gene was connected to the CaMV 35S promoter in the ordinary direction, was selected from the recombinant plasmids and designated as pBIsRS1.

Each of the plasmids obtained as described above was introduced into *Agrobacterium* LBA4404 by means of triparental mating of *Escherichia coli* HB101 containing the plasmids and *Agrobacterium* LBA4404.

<2> Transformation

*Arabidopsis thaliana* was transformed as follows. Seeds of *Arabidopsis thaliana* was subjected to a treatment for water absorption. After that, they were sterilized by treating them with 80% ethanol containing 1% Tween 20 for 5 minutes, and treating them with 10% sodium hypochlorite solution also containing 1% Tween 20 for 10 minutes, followed by washing five times with sterilized water. The seeds were suspended in 1% low melting point agarose, and they were spread over an MS medium (MS basic medium (Murashige and Skoog, *Physiologia Plantrum,* 15, 473-497 (1962)), B5 vitamin, 10 g/L sucrose, 0.5 g/L MES, pH 5.8). The seeds were cultivated at 22° C. for 1 week in a culture room to give a cycle comprising light irradiation for 16 hours and darkness for 8 hours. Plants with seed leaves expanded were subjected to setting with rock wool. Cultivation was continued under the same condition. After about 3 weeks, decapitation was performed when the plants caused bolting to have stems of heights of several centimeters. The plants were allowed to grow until a state in which first flowers bloom on elongated branches 1 week after the decapitation.

*Agrobacterium* harboring the introduced recombinant plasmid containing the raffinose synthase gene was precultivated in 2 ml of LB medium. An obtained culture was inoculated into LB medium containing 50 mg/L kanamycin and 25 mg/L streptomycin, followed by cultivation at 28° C. for about 1 day. Bacterial cells were collected at room temperature, and they were suspended in a suspension medium for infiltration (½ MS salt, ½ Gamborg B5 vitamin, 5% sucrose, 0.5 g/L MES, pH 5.7 (KOH), to which, immediately before the use, benzylaminopurine was added to give a final concentration of 0.044 μM, and Silwet L77 was added in an amount of 200 μl per liter (final concentration: 0.02%)) so that $OD_{600}$ of an obtained bacterial suspension was 0.8.

Flowers in bloom and fructification were removed from the plants to be subjected to infiltration. The rock wool was inverted upside down, and flowers which were not in fructification were immersed in the suspension of *Agrobacterium*, followed by being placed in a desiccator so that the pressure was reduced to be 40 mmHG for 15 minutes. Seeds were harvested after 2 to 4 weeks. The harvested seeds were stored in a desiccator.

Next, transformants were selected on a selection medium. The seeds were sterilized in the same manner as described above, and they were cultivated on a selection medium (MS salt, Gamborg B5 vitamin, 1% sucrose, 0.5 g/L MES, pH 5.8, 0.8% agar, to which antibiotics for selection, i.e., carbenicillin (final concentration: 100 mg/L) and kanamycin (final concentration: 50 mg/L) were added after autoclaving)) at 22° C. to select resistant plants. The resistant plants were transferred to a fresh medium, and they were allowed to grow until true leaves expanded. Seeds were harvested from the obtained plants. Selection was repeated in the same manner as described above, and thus T3 seeds were obtained. The T3 seeds were measured for the raffinose content in accordance with the method described above. Results are shown in Table 3.

TABLE 3

| Plant | Raffinose content (mg/g) |
|---|---|
| Wild type | 0.20 |
| Transformant (pBIcRS1) | 0.00 |
| Transformant (pBIcRS9) | 0.00 |
| Transformant (pBIsRS1) | 0.22 |

INDUSTRIAL APPLICABILITY

The present invention provides the purified raffinose synthase, the raffinose synthase gene, the chimeric gene comprising the raffinose synthase gene and the regulatory region expressible in plants, and the plant to which the chimeric gene is introduced.

Raffinose can be efficiently synthesized from sucrose and galactinol by using the raffinose synthase of the present invention. The content of the raffinose family oligosaccharides in plants can be changed by utilizing the raffinose synthase gene or the chimeric gene of the present invention.

What is claimed is:

1. An isolated raffinose synthase having an activity to produce raffinose from sucrose and galactinol and comprising SEQ ID NO: 5.

2. The raffinose synthase of claim 1, which consists of SEQ ID NO: 5.

3. The raffinose synthase of claim 1, which has the following properties:
   (1) action and substrate specificity: produces raffinose from sucrose and galactinol;
   (2) optimum pH: about 6 to 8;
   (3) optimum temperature: about 35 to 40° C.;
   (4) molecular weight:
      (i) about 75 kDa to 95 kDa estimated by gel filtration chromatography;
      (ii) about 90 kDa to 100 kDa estimated by polyacrylamide gel electrophoresis; and
      (iii) about 90 kDa to 100 kDa estimated by SDS-polyacrylamide gel electrophoresis under a reduced condition; and
   (5) inhibition: inhibited by iodoacetamide, N-ethylmaleimide, and myo-inositol.

4. The raffinose synthase of claim 3, which is isolated from cucumber.

5. A method for producing raffinose, comprising the step of allowing the raffinose synthase as defined in claim 1 to act on sucrose and galactinol to produce raffinose.

6. A method for producing raffinose, comprising the step of allowing the raffinose synthase as defined in claim 2 to act on sucrose and galactinol to produce raffinose.

7. A method for producing raffinose, comprising the step of allowing the raffinose synthase as defined in claim 3 to act on sucrose and galactinol to produce raffinose.

8. A method for producing raffinose, comprising the step of allowing the raffinose synthase as defined in claim 4 to act on sucrose and galactinol to produce raffinose.

* * * * *

UNITED STATES PATENT AND TRADEMARK OFFICE
CERTIFICATE OF CORRECTION

| | | |
|---|---|---|
| PATENT NO. | : 7,455,996 B2 | Page 1 of 1 |
| APPLICATION NO. | : 11/034848 | |
| DATED | : November 25, 2008 | |
| INVENTOR(S) | : Osumi et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 987 days.

Signed and Sealed this
Sixth Day of November, 2012

David J. Kappos
*Director of the United States Patent and Trademark Office*